(12) United States Patent
Ramaekers

(10) Patent No.: US 6,962,718 B2
(45) Date of Patent: Nov. 8, 2005

(54) COMPOSITIONS FOR TREATING ANIMAL DISEASES AND SYNDROMES

(76) Inventor: Joseph C. Ramaekers, 555 Charlson Rd., Aptos, CA (US) 95003

(*) Notice: Subject to any disclaimer, the term of this patent is extended or adjusted under 35 U.S.C. 154(b) by 0 days.

(21) Appl. No.: 10/136,854

(22) Filed: Apr. 30, 2002

(65) Prior Publication Data

US 2003/0077254 A1 Apr. 24, 2003

Related U.S. Application Data

(63) Continuation-in-part of application No. 09/847,036, filed on Apr. 30, 2001, now Pat. No. 6,506,413.

(51) Int. Cl.[7] .................. A61K 35/20; A61K 35/72; A61K 35/74; A61K 35/78
(52) U.S. Cl. .................. 424/535; 424/520; 424/400; 424/725; 424/93.4; 424/93.51
(58) Field of Search .................. 424/520, 535, 424/400, 725, 93.4, 93.51, 130.1, 134.1, 529, 184.1; 514/2

(56) References Cited

U.S. PATENT DOCUMENTS

| | | | |
|---|---|---|---|
| 4,220,666 A | * | 9/1980 | Fields .................. 426/62 |
| 4,237,118 A | * | 12/1980 | Howard .................. 424/630 |
| 4,435,384 A | | 3/1984 | Warren |
| 4,816,563 A | | 3/1989 | Wilson et al. |
| 5,080,895 A | | 1/1992 | Tokoro |
| 5,185,166 A | * | 2/1993 | Nakagawa et al. .................. 426/74 |
| 5,211,956 A | * | 5/1993 | Sawai et al. .................. 424/451 |
| 5,234,698 A | | 8/1993 | Fahim |
| 5,753,696 A | * | 5/1998 | Shealy et al. .................. 514/474 |
| 5,759,543 A | * | 6/1998 | Morozova et al. .................. 424/123 |
| 5,840,700 A | | 11/1998 | Kirkpatrick et al. |
| 5,883,224 A | | 3/1999 | Kirkpatrick et al. |
| 6,287,576 B1 | * | 9/2001 | Bgatov et al. .................. 424/400 |

FOREIGN PATENT DOCUMENTS

CN  1093267 A  * 10/1994

OTHER PUBLICATIONS

Jenness, "The composition of milk", Semin Perinatol., 1979, 3(3):225–39.*
Harman, J., and Ward, M., The Role of Nutritional Therapy in the Treatment of Equine Cushing Syndrome and Laminitis, Alternative Medicine Review, 6(Supp), S4–S16, (2001).
Kahn, A et al., Transfer Factor in the Treatment of Herpes Simplex Types 1 and 2 Dermatologica, 163(2), 177–85 (1981).
McMeeking, A et al., A controlled trial of bovine dialyzable leukocyte extract for cryptosporidiosis in patients with AIDS, J. Infect. Disease, 161(1), 108–12 (1990).
Steele, RW et al., Transfer factor for the prevention of varicella–zoster infection in childhood leukemia, N. Engl. J. Med., Aug. 14, 303(7), 355–59 (1980).
Viza, D. et al., Use of specific transfer factor for the prevention or the treatment of herpes infections in mice and in man, J. Exp. Pathology, 3(4), 407–20.

* cited by examiner

Primary Examiner—Leon B. Lankford, Jr.
Assistant Examiner—Ruth A. Davis
(74) Attorney, Agent, or Firm—Richard F. Trecartin; Dorsey & Whitney LLP

(57) ABSTRACT

Various compositions containing transfer factor in combination with nutraceuticals are provided including transfer factor in combination with zinc and essential fatty acids and transfer factor in combination with lactic acid generating bacteria. Also provided are methods for treating animal diseases and syndromes using these compositions.

15 Claims, No Drawings

COMPOSITIONS FOR TREATING ANIMAL DISEASES AND SYNDROMES

CROSS-REFERENCE

This application is a continuation-in-part of application Ser. No. 09/847,036, filed Apr. 30, 2001 now U.S. Pat. No. 6,506,413.

FIELD OF THE INVENTION

This invention relates to compositions of transfer factor in combination with specific nutraceuticals and to the use of these compositions in treating diseases and syndromes.

BACKGROUND OF THE INVENTION

Transfer factor which is produced by leucocytes and lymphocytes are small water soluble polypeptides of about eight amino acids and also associated cofactors that stimulate or transfer cell mediated immunity from one individual to another and across species. Since transfer factors are smaller than antibodies, they do not transfer antibody mediated responses nor do they induce antibody production. The properties, characteristics and processes for obtaining transfer factor or transfer factors are discussed in U.S. Pat. Nos. 4,816,563; 5,080,895; 5,840,700 and 5,883,224, the contents of which are hereby incorporated by reference into the present application. Transfer factor preparations have been demonstrated to contain three types of immune modulation activities. The inducer and suppressor activities are considered general and non-specific resulting in overall enhancement of immune responsiveness through interactions with the T-helper and T-suppressor cells.

Transfer factor has been described as an effective therapeutic for Herpes simplex virus (Viza, et al.), a treatment for acne blemishes, U.S. Pat. No. 4,435,384 and as a treatment against *C. albicans* (Khan et al.). Transfer factor has also been used to treat intestinal cryptosporidiosis in recipients treated with specific transfer factor (McMeeking, et al.). Still, et al. also showed that chicken pox infections were prevented by pretreatment of children treated with transfer factor from individuals that had chicken pox or who in other words had been sensitized to the varicella antigen. The antigen specific transfer factors are the most well studied and have been demonstrated to be able to convey the antigen recognition ability of the experienced donor to the naive recipient. It may be assumed that the individual or animal that is the source of the transfer factor has been sensitized to the antigen of interest. The term antigen is defined herein is anything that will initiate the cell mediated immune response. However, transfer factor as found in commercial bovine colostrum extract coming from a pool of animals (e.g., cows) contains the acquired immunity from all of the pool and therefore provides a type of generalized adoptive transfer of immunity. Transfer factors or transfer factor can be obtained from a dialyzable extract of the lyzed cells or from an extract of extracellular fluid containing transfer factor. Common sources of transfer factors are colostrum, ova, blood and milk. It is common practice to refer to preparations that contain transfer factor by the name of the active component (i.e., transfer factor or TF). Transfer factor extract containing transfer factors is also herein referred to as transfer factor. Transfer factor from bovine colostrum extract is defined as defatted water soluble material from colostrum that will pass through a nominal 10,000 molecular weight filter. The colostral derived transfer factor has been prepared with activity against various organisms including infectious bovine rhinotracheitis virus. One of the specific effects of transfer factor is a significantly increased natural killer (NK) cell activity. Natural killer cells provide protection against viruses as part of the innate immune defense system.

The use of nutraceuticals to treat vitamin and mineral deficiencies is well known. However, the use of nutraceuticals, such as vitamins, minerals and other nutritional components to prevent and treat diseases other than those caused by the deficiency of those nutraceuticals, though still controversial, is receiving more consideration from both laymen and physicians. The following is a list of nutraceuticals and some of their generally acknowledged nutritional and health benefits.

Vitamin A—is important in preventing eye epithileol disorders; deficiency results in night blindness Vitamin $B_2$—is essential to human nutrition relating to the oxidation of carbohydrates and amino acids Mixed tocopherols—are antioxidants Choline Chloride—is a member of the vitamin B complex and a dietetic factor for furnishing free methyl groups for transmethylation Vitamin $B_6$—functions in the formation and breakdown of amino acids and is involved in the synthesis of serotonin and norepinephrine. However, exact dietary requirements are uncertain Vitamin $B_{12}$—is an antipernicious-anemia factor essential for normal hemopoiesis Vitamin E—is an antioxidant that protects against free radicals.

Vitamin K—is essential for the formation of prothrombin

Biotin—functions in metabolic processes leading to the formation of fats and utilization of carbon dioxide Folic Acid—a growth factor involved in the formation of nucleic acids and necessary for the formation of heme Niacin—a component of the Vitamin B complex, a deficiency results in pellagra Vitamin $D_3$—is important in the absorption of calcium Pantothenic Acid—is considered essential for growth and well being of animals; deficiency results in growth retardation, skin lesions and graying of hair Thiamine—is necessary in diet of all animals except ruminants; used to prevent beriberi and important in carbohydrate metabolism Lysine—is an essential amino acid Methionine—is a sulfur containing essential amino acid Arginine—is an amino acid important in the synthesis of urea (principal form in which mammals excrete)

Soy—is a source of proteins

Methyl Sulfonyl Methane—is a form of organic sulfur involved in cell membrane permeability Zinc—is an essential mineral for growth; deficiency creates susceptibility to various pathogens Omega 3-, 6-, and 9-Fatty Acids—are essential fatty acids and polyunsaturated fats; a deficiency results in hypertension and high blood pressure; they are believed to improve immune function Yeast—(e.g., brewers, bakers, etc.) contains beta glucans which appear to increase production and/or activation of natural killer cells Calcium—is required for bone development Phosphorus—is required for bone development Selenium—a deficiency results in heart muscle disease Iron—is required for formation of hemoglobin; deficiency results in anemia Magnesium—is an element required for growth in all living organisms Manganese—is an element required for growth in all living organisms Copper—is an element required for growth in plants, animals and most microorganisms Iodine—is an element necessary for the synthesis of hormone production by the thyroid gland Cobalt—is a trace element essential in the nutrition of ruminants (cattle, sheep) and in the maturation of human red blood cells in the form of Vitamin $B_{12}$ Molybdenum—is a trace element believed to be necessary in animal diets but its function in the minimal levels have not been established Lactic Acid Generating Bacteria—are a digestive aid and growth inhibitor of harmful bacteria Chrondroitin—is a component of connective tissue which may relieve joint pain and arthritis.

Glucosamine—is a component of micropolysaccharides and glycoprotein which may be helpful in arthritis.

Di-methyl glycine—is a methylated amino acid found in all cells and an antioxidant.

Montmorillonite—is collodial clay containing trace elements which are considered by some to be important for well being and to compensate for elements no longer in foods because of depleted soils (the components are shown below in Table 1)

Super oxide dismutase (SOD)—is an antioxidant enzyme present in the mammalian body. It converts super oxide free radicals to the less active peroxide. It stimulates hair growth and is believed to protect cells against ultraviolet-B irradiation and to protect the heart.

*Boswellia*—is an herb *Boswellia serrata*. Boswellic acids, the biologically active ingredients of the gum resin of this herb, are considered to have anti-inflammatory and anti-arthritic actions.

Octocosonol—is derived from wheat germ oil and provides 17% more residual energy before fatigue.

TABLE 1

Montmorillonite Components
Average Nutrient Content Per Ounce
(1 Tablespoon = ~0.36 oz.)
(mg)

| Silicon | 6933 | Tungsten | 0.218 |
| --- | --- | --- | --- |
| Aluminum Silica | 2505 | Vanadium | 0.215 |
| Sodium Chloride | 1320 | Ruthenium | 0.210 |
| Potassium | 1293 | Baron | 0.189 |
| Protein | 1116 | Bromine | 0.140 |
| Calcium | 1104 | Cobalt | 0.129 |
| Sulfur | 431 | Selenium | 0.110 |
| Iron | 431 | Syprosium | 0.107 |
| Magnesium | 224 | Fluorine | 0.102 |
| Chlorine | 164 | Scandium | 0.0997 |
| Titanium | 61.9 | Samarium | 0.0943 |
| Carbon | 48.2 | Nobelium | 0.0754 |
| Sodium | 37.2 | Copper | 0.0593 |
| Barium | 10.5 | Praseodymium | 0.0539 |
| Phosphate | 8.62 | Erbium | 0.0539 |
| Strontium | 6.46 | Hafnium | 0.0539 |
| Cesium | 4.93 | Ytterbium | 0.0377 |
| Manganese | 4.04 | Lithium | 0.0377 |
| Thorium | 2.69 | Yttrium | 0.0323 |
| Uranium | 2.69 | Holmium | 0.0296 |

TABLE 1-continued

Montmorillonite Components
Average Nutrient Content Per Ounce
(1 Tablespoon = ~0.36 oz.)
(mg)

| Arsenic | 1.97 | Cadmium | 0.0296 |
| --- | --- | --- | --- |
| Chromium | 1.89 | Palladium | 0.0189 |
| Molybdenum | 1.64 | Terbium | 0.0161 |
| Nickel | 1.62 | Thulium | 0.0161 |
| Iodine | 1.28 | Gold | 0.0161 |
| Lead | 1.17 | Tantalum | 0.0135 |
| Cerium | 1.08 | Iridium | 0.0135 |
| Rubidium | 0.983 | Lutetium | 0.0108 |
| Antimony | 0.781 | Europium | 0.0108 |
| Gallium | 0.673 | Rhodium | 0.0108 |
| Germanium | 0.673 | Tin | 0.0108 |
| Neodymium | 0.539 | Silver | 0.00808 |
| Zinc | 0.539 | Indium | 0.00808 |
| Lanthanum | 0.486 | Oxygen | 0.00539 |
| Bismuth | 0.385 | Mercury | 0.00269 |
| Zirconium | 0.269 | Tellurium | 0.00269 |
| Rhenium | 0.269 | Beryllium | 0.00269 |
| Thallium | 0.269 | | |

Allopathic medicine is usually used to treat animal diseases. Unfortunately, such medicines often have serious side effects such as nausea, gastritis, diarrhea, maladsorption of vitamins, circulation and respiratory problems and allergic reactions. For example, Cushings disease, a fairly common physiological abnormality in ungulates, particularly horses, manifests itself as a pituitary adenoma that results in erratic cortisol and insulin levels. Cushings syndrome, however, is defined as a cortisol excess regardless of the cause. Clinical signs are frequent urination, polydypsia, failure to shed hair and poor hair coat, lack of muscle tone and sometimes poor coordination. The common allopathic drugs for treating Cushings disease and/or Cushings syndrome are Parlodel (bromocreptine mesylate) a dopamine agonist, cyproheptadine a serotonin blocker, and Permax (pergolide mesylate) another dopamine agonist. However, in oral form Parlodel has poor absorption and the intra molecular injectible form which needs to be given twice a day is impractical. Cyproheptadine usually takes about six to eight weeks and since it is a serotonin antagonist it can effect other systems in the brain. Permax is also an intense vasoconstrictor and can worsen chronic laminitis which is common with Cushings.

Onchocerciasis is a disease resulting from infection from microfilariae spread by flies and is characterized by fibrous nodules in the skin and subcutaneous tissues. The usual treatment is the anthelcide Ivermectin, yet the autoimmune component of this disease remains to the extent that there are constant relapses. Cortisone and antibiotics are also used. However, both of these drugs can be extremely toxic and often cause allergic reactions. Use of cortisone can also cause a depressed immune response, demineralization and eroding of the sensitive lamina of the hoof wall.

Circo virus is a disease affecting pigeons with a 10% mortality rate. The immune defense of the birds is reduced in a manner similar to that caused by an immune deficiency virus or mycoplasma causing susceptibility to other infections. There are approximately 30,000 racing pigeons this disease can affect and known treatments are not very effective.

Equine protozoal myelitis that results in severe inflamation of the spinal chord or of the bone marrow is usually treated with Pyrimethamine (an antibiotic), sulfadiazine (an antibiotic) and Trimethoprim sulfur (an antibiotic).

PURRS (porcine upper respiratory and reproductive disease in swine) disease is the most devastating problem in the swine industry costing the industry millions in loss, from morbidity, mortality, and infertility in swine. It is usually treated with antibiotics. However, these treatments are costly.

Livestock, especially horses and cows, often suffer from ulcers, including stomach ulcers and ulcerations and inflammation of the joints. The ulcers and ulcerations are usually treated with strong antibiotics and cortisones which again can cause allergic reactions, fever and other severe side effects. Also, the use of antibiotics to treat animals especially livestock food source animals often results in resistance to those antibiotics which is becoming a serious health problem with respect to all animals including humans. Inflammation such as laminitis in horses is usually treated with NSAID (non-steroidal antiinflamatory drug), compositions which again sometimes have serious side effects such as kidney and liver complications. Use of NSAID compositions such as Butazolidin, Banamine, Rymadal, Etogesic and aspirin often cause ulcers in the digestive system allowing toxins from the gut to enter the abdominal cavity and blood stream. This condition is known as leaky bowel or gut syndrome and often aggravates the original inflammation that initiated the treatment. In horses with laminitis, where one is trying to eliminate the flow of toxins to the sensitive lamina in the horse's hoof wall, the development of leaky gut syndrome is obviously counterproductive.

Diseases fairly common in domestic pets are feline leukemia in a cat and flea bite dermatitis in numerous animals such as cats, dogs, etc. Feline leukemia can be treated with various current oncological drugs but they are very expensive. Treatment of flea bite dermatitis in animals usually involves antibiotics and prednisone which is often ineffective and use of prednisone can cause sodium retention, eye problems and heart failure.

Strangles, a disease in horses caused by *Streptococcus equi* that forms abscesses in the lymph nodes and other parts of the body, is usually treated by rest and antibiotic therapy. The disease spreads quickly and is difficult to prevent. The disease can also cause chronic life-long mononucleosis-like symptoms in the horse.

Many animals such as dogs and livestock (horses, cows, sheep, etc.) suffer from chronic coughs believed to be caused by dust allergens. While seldom fatal, the ailment can lead to serious complications such as secondary infections. The cough which is often confused with other upper respiratory infections is usually treated with antibiotics such as Trimethoprim sulfur and expectorants. However, such treatment is often ineffectual.

Lymphopenia and hypothyroidism also occur in livestock. Lymphopenia is a decrease in the number or proportion of lymphocytes in the circulating blood which often leads to an increased susceptibility to bacterial and fungal infections. This hematologic abnormality can result from hereditary diseases, impaired production because of bone marrow cancer, but often the result of the impairment of cell production by drugs such as cancer drugs, antithyroid drugs, phenothyoscenes, penicillin, and other antibiotics. Again, treatment usually involves broad spectrum antibiotic therapy which again can lead to antibiotic resistance or other physiological problems.

Hypothyroidism in livestock and often domestic animals frequently occurs for unknown reasons. Treatment often involves replacement therapy with synthetic preparations of thyroxine. However, long-term replacement therapy can result in heart problems and bone diseases such as osteoporosis.

Another very serious problem with farm animals is high morbidity (i.e., sickness) among young animals which can result in severe financial losses to farmers and ranchers. The current methods of controlling morbidity involve a standard oat or grain diet for livestock and fowl, and inoculations and antibiotics.

In young cattle (stockers), this problem is particularly significant. The weaning, processing and transport of stockers is known to be very stressful and often leads to high morbidity and mortality rates due to bovine respiratory disease (BRD). In a six year study over 15% of stocker cattle exhibited BRD. Approximately 70% of feedlot death losses are attributable to BRD. Death losses are often not the largest costs. Weight loss, lower daily gain, carcass degradation, medicine costs and drug residues in the carcass can amount to $50.00–$100.00 per animal without death loss.

The observation of clinical signs of BRD and removal of calves was only poorly correlated with the presence of lung lesions at the time of slaughter. On the other hand, the drop in frequency and duration of eating and drinking are good indicators of BRD, as evidenced by the presence of lung lesions at time of slaughter. The dry matter feed intake for calves during the first 28 days in the feedlot has been shown to be 32% less in sick calves than in their well counterparts; additionally the average daily weight gain during this period was 0.01 Kg (0.02 lbs) vs 0.59 Kg (1.3 lbs) respectively. Thus nutritional interventions must take into account that the calves which are most sick are the ones who are least likely to obtain the nutrition they need through top dressing of feed.

Preconditioning of calves by vaccinating, bunk breaking them prior to weaning, and/or prophylactic administration of antibiotics often reduces the morbidity and mortality during the initial 2–4 weeks following transporting to a new premises. The inability of the rancher to recover the costs associated with preconditioning has inhibited the adoption of these practices.

There are incidences where preconditioned calves succumb to BRD sickness at rather high rates. This might result from neutralization of the administered vaccines by residual maternal antibodies. A second reason may be that the administered vaccines do not correspond to the initiating viral agents. Historically bovine rhinotracheitis (IBR) virus, bovine viral diarrhea (BVD) virus, parainfluenza virus type 3 (PIV-3), and bovine respiratory syncytial virus (BRSV) have been seen as the initiating agents of BRD. Recent evidence has established that bovine coronavirus must also be added to the list of potential initiating viral infections.

A third reason may be that the bacterial component of BRD, such as *Pasteurella haemolytica* or *Pasteurella multocida*, may be resistant to the administered antibiotics. A final reason, which may encompasses all others, is the inability of the calves' innate or acquired immunity to adapt under the increased stress of weaning, processing, and transport.

It is well established that good nutrition strengthens immunity in cattle. The common addition of immune stimulant nutrients such as zinc and vitamin E to the diet of stocker cattle provides essential building blocks for building a strong immune defense. Nevertheless the published BRD nutritional intervention studies have not been consistently positive indicating that an unidentified deficiency still existed in the formulations studied.

Since most of the common medical treatments for the numerous medical problems discussed above and on the preceding pages can involve serious side effects, compositions containing natural products and nutraceuticals that would treat these diseases and syndromes with less contraindications and diminish the development of antibiotic resistance are highly desirable, not only to relieve suffering in the animals but also to improve the quality of meat and human health.

SUMMARY OF THE INVENTION

This invention provides formulations of transfer factor in combination with minerals, antioxidants, amino acids and other nutraceuticals preferably administered orally to treat animals exhibiting disease symptoms but also to lower general morbidity.

Accordingly, one aspect of this invention provides a formulation comprising transfer factor, zinc and at least one essential fatty acid.

A second aspect of the invention is to provide a formulation of transfer factor, zinc, at least one essential fatty acid, vitamin C and yeast.

A third aspect of the invention is to provide a formulation of transfer factor, zinc, at least one essential fatty acid, vitamin C, yeast, ionic salts or chelates of the elements calcium, phosphorous, selenium, iron, magnesium, manganese, copper, iodine, cobalt and molybdenum.

A fourth aspect of the invention is to provide a formulation of lactic acid generating bacteria, yeast, montmorillonite, vitamins A, $B_2$, $B_6$, $B_{12}$, E and K, biotin, folic acid, niacin, vitamin $D_3$, pantothenic acid, thiamine, lysine, methionine, arginine and methyl sulfonyl methane.

A fifth aspect of the invention is to provide a formulation comprising transfer factor, zinc, at least one essential fatty acid, vitamin C, yeast and ionic salts or chelates of the elements calcium, phosphorous, selenium, iron, magnesium, manganese, copper, iodine, cobalt and molybdenium.

Another aspect of the invention is to provide a formulation of transfer factor, zinc, at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, $B_{12}$, E and K.

A further aspect of the invention is to provide a formulation of transfer factor and lactic acid generating bacteria.

Yet another aspect of the invention is to provide a formulation of transfer factor, zinc at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, B12, E and K, biotin, folic acid, niacin, vitamin $D_3$, pantothenic acid and thiamine.

Still another aspect of the invention is to provide a formulation comprising transfer factor, zinc, at least one essential fatty acid, vitamin C, ionic salts or chelates of the elements calcium, phosphorous, selenium, iron, magnesium, manganese, copper, iodine, cobalt and molybdenum, lactic acid generating bacteria, yeast, montmorillonite and vitamins A, $B_2$, $B_6$, $B_{12}$, E and K, and biotin, folic acid, niacin, vitamin $D_3$, pantothenic acid, thiamine, lysine, methionine, arginine, and methyl sulfonyl methane.

In yet another aspect, the invention provides the method of treating Cushing syndrome, Cushings disease, adenomas and other benign tumors, onchocerciasis or equine protozoal myelitis in an animal comprising administering to the animal a formulation of transfer factor, zinc and at least one essential fatty acid in an amount and at a frequency and for a duration effective to decrease or eliminate the tumors or the symptoms of those diseases.

A further aspect of the invention is to treat Cushing syndrome, Cushings disease, adenomas, onchocerciasis, hypothyroidism or equine protozoal myelitis by administering to the animal a formulation of transfer factor, zinc and at least one essential fatty acid in combination with nutraceuticals selected from the group consisting of vitamin C, ionic salts or chelates of the elements calcium, phosphorous, selenium, iron, magnesium, manganese, copper, iodine, cobalt and molybdenum, lactic acid generating bacteria, yeast, montmorillonite, vitamins A, $B_2$, $B_6$, $B_{12}$, E and K, and biotin, folic acid, niacin, vitamin $D_3$, pantothenic acid, lysine, methionine, arginine and methyl sulfonyl methane. The preferred formulation for treating these diseases includes all of the nutraceuticals.

Still a further aspect of the invention is a method of treating inflamation and ulcers in an animal comprising administering to the animal in an amount at a frequency and for a duration effective to reduce or eliminate the symptoms of the inflamation or ulcers a formulation comprising transfer factor and lactic acid generating bacteria.

Yet another aspect of this invention is a method of treating inflamation and ulcers in an animal comprising administering to the animal a formulation of transfer factor and other nutraceuticals selected from the group consisting of zinc, methyl sulfonyl methane, lactic acid generating bacteria, yeast, at least one essential fatty acid, vitamin C, ionic salts or chelates of the elements calcium, phosphorous, selenium, iron, magnesium, manganese, copper, iodine, cobalt and molybdenum, montmorillonite, vitamins A, $B_2$, $B_6$, $B_{12}$, E and K, and biotin, folic acid, niacin, vitamin $D_3$, pantothenic acid, thiamine, lysine, methionine and arginine and mixtures thereof in an amount, at a frequency and for a duration effective to reduce or eliminate the symptoms of the inflamation or ulcers.

Still yet another aspect of the invention provides for a formulation comprising transfer factor and a lactic acid generating bacteria.

Yet another aspect of the invention is to provide a formulation, comprising a transfer factor, lactic acid generating bacteria and zinc.

Still a further aspect of the invention is to provide for a formulation comprising transfer factor, lactic acid generating bacteria, and montmorillonite.

Still another aspect of the invention is a formulation comprising transfer factor, lactic acid generating bacteria, zinc, montmorillonite, at least one essential fatty acid, ionic salt or chelates of the elements calcium, phosphorous, selenium, iron, magnesium, manganese, copper, iodine, cobalt and molybdenum, yeast, vitamins A, $B_2$, $B_6$, $B_{12}$, C, E and K, biotin, folic acid, niacin, vitamin $D_3$, pantothenic acid, thiamine, lysine, methionine, arginine and methyl sulfonyl methane.

Another aspect of this invention provides for a method of treating flea bite dermatitis in an animal or feline leukemia in a cat comprising administering to the animal or cat a formulation of transfer factor and lactic acid generating bacteria in an amount and at a frequency and for a duration effective to reduce or eliminate the symptoms of the dermatitis or leukemia.

Still a further aspect of the invention provides for a method of treating flea bite dermatitis in an animal or feline leukemia in a cat comprising administering to the animal or cat the formulation comprising transfer factor, lactic acid generating bacteria, zinc, montmorillonite, at least one essential fatty acid, ionic salt or chelates of the elements calcium, phosphorous, selenium, iron, magnesium, manganese, copper, iodine, cobalt and molybdenum, yeast, vitamins A, $B_2$, $B_6$, $B_{12}$, C, E and K, biotin, folic acid, niacin, vitamin $D_3$, pantothenic acid, thiamine, lysine, methionine, arginine, and methyl sulfonyl methane in an amount and at a frequency and for a duration effective to reduce or eliminate symptoms of the dermatitis or leukemia.

A further aspect of the invention is to provide a method of treating strangles, chronic dust allergen cough or hypothyroidism in an animal comprising administering to the animal a formulation of transfer factor and a lactic acid generating bacteria in an amount and at a frequency and for a duration effective to reduce or eliminate the symptoms of the strangles, chronic dust allergen cough or hypothyroidism.

Still another aspect of the invention is a method of treating lymphopenia in an animal comprising administering to the animal a formulation of transfer factor and a lactic acid generating bacteria in an amount, at a frequency and for a duration effective to reduce or eliminate the symptoms of the lymphopenia.

Still a further aspect of the invention is a method of reducing morbidity in young livestock animals comprising administering to the animals a formulation of transfer factor and a lactic acid generating bacteria in a amount, at a frequency and for a duration effective to achieve a reduction in morbidity as compared to controls.

Yet another aspect of the invention is to provide a formulation comprising transfer factor, lactic acid generating bacteria, ionic salts or chelates of the elements calcium, magnesium, sodium and potassium, citric acid, vitamins A, $B_2$, $B_6$, $B_{12}$, C and E, and yeast.

Still another aspect of this invention is a method of treating strangles, chronic dust allergen cough or hypothyroidism in an animal comprising administering to the animal a formulation of transfer factor and lactic acid generating bacteria and other nutraceuticals selected from the group consisting of ionic salts or chelates of the elements calcium, magnesium, sodium and potassium, citric acid, vitamins A, $B_1$, $B_2$, $B_6$, $B_{12}$, C and E, and yeast. The preferred formulation comprises transfer factor, lactic acid generating bacteria and all of these other nutraceuticals.

A further aspect of the invention is to provide a formulation of transfer factor and super oxide dismutase.

Another aspect of the invention is to provide a formulation of transfer factor and at least one glucosamine salt.

Still a further aspect of the invention is to provide a formulation of transfer factor, super oxide dismutase and at least one glucosamine salt.

Yet a further aspect of the invention is to provide a formulation of transfer factor, super oxide dismutase, at least one glucosamine salt and chondroitin.

Yet an additional aspect of the invention is to provide a formulation of transfer factor, super oxide dismutase, at least one glucosamine salt, chondroitin and glycine.

Still an additional aspect of the invention is to provide a formulation of transfer factor, super oxide dismutase, at least one glucosamine salt, chondroitin, glycine and methyl sulfonyl methane.

Another aspect of the invention is to provide a formulation of transfer factor, super oxide dismutase, at least one glucosamine salt, chondroitin, glycine, methyl sulfonyl methane and boswellic acids.

Another aspect of the invention is to provide a formulation of transfer factor, super oxide dismutase, at least one glucosamine salt, chondroitin, glycine, methyl sulfonyl methane, boswellic acids and octocosonol.

Another aspect of the invention is to provide a formulation of transfer factor, super oxide dismutase, at least one glucosamine salt, chondroitin, glycine, methyl sulfonyl methane, boswellic acids, octocosonol and montmorillinite.

Still a further aspect of the invention is to treat or cure inflammation, arthritis or laminitis with a formulation of transfer factor and super oxide dismutase.

Yet a further aspect of the invention is to treat or cure inflammation, arthritis or laminitis with a formulation of transfer factor and glucosamine salts.

Another aspect of the invention is to treat or cure inflammation, arthritis or laminitis with a formulation of transfer factor, super oxide dismutase and glucosamine salts.

Another aspect of the invention is to treat or cure inflammation, arthritis or laminitis with a formulation of transfer factor, glucosamine salts, super oxide dismutase, glycine, methyl sulfonyl methane, octocosonol and montmorillinite.

Yet a further aspect of the invention is a method of treating lymphopenia in an animal comprising administering to the animal a formulation of transfer factor and lactic acid generating bacteria and other nutraceuticals selected from the group consisting of ionic salts or chelates of the elements calcium, magnesium, sodium, potassium and zinc, citric acid, vitamins A, $B_1$, $B_2$, $B_6$, $B_{12}$, C and E, and yeast. The preferred formulation comprises transfer factor, a lactic acid generating bacteria and all of these other nutraceuticals.

Still yet another aspect of the invention is a method of reducing morbidity in young livestock animal comprising administering to the animals a formulation of transfer factor and lactic acid generating bacteria and nutraceuticals selected from the group consisting of ionic salts or chelates of the elements calcium, magnesium, sodium and potassium, citric acid, vitamins A, $B_1$, $B_2$, $B_6$, $B_{12}$, C and E, and yeast. The preferred formulation comprises transfer factor, a lactic acid generating bacteria and all of these other nutraceuticals.

Other aspects of the invention will become apparent to the skilled artisan by the following description of the invention.

DETAILED DESCRIPTION OF THE INVENTION

In accordance with this detailed description, the following definitions and abbreviations apply.

Nutraceuticals—Nutrients used to treat or prevent a disease or syndrome.

Pharmaceutically acceptable—meant that the substance in the dose and form given is not known to cause serious side effects and harm apart from an occasional allergic reaction. In general, as used herein, the term pharmaceutically acceptable has the same meaning as the common meaning for that term. However, the substance need not be pharmaceutically acceptable for humans unless the recipient is human. Nevertheless, it must be relatively safe for the animal receiving the substance.

EPM—Equine protozoal myelitis.

Various forms of transfer factor may be used in accordance with this invention. They include excreted transfer factor released from transfer factor containing cells such as lymphocytes and leukocytes, and collected from extracellular fluids such as colostrum, blood and milk. Another form includes preexcreted transfer factor found within the cell or on the cell surface. Also substantially pure transfer factor defined as ribonuclease resistant polyribonucleotides having a molecular weight of less than 10,000 daltons and a specific activity of at least 5000 units per adsorbance unit at 214 nM may also be used but is not necessary for the results achieved in the course of this invention. The invention may also use transfer factor specific for an antigen obtained by collecting transfer factor from an animal that has been exposed to that antigen. An example of such an antigen may be *Streptococcus equi*. The transfer factor used in the Examples of this invention and referred to in the following Tables and further referred to in the rest of the detailed description is extracted from colostrum collected from a general pool of lactating cows. The transfer factor, as used in the Examples, Tables and the following description, is further defined as defatted water soluble material from bovine colostrum that will pass through a nominal 10,000 molecular weight filter. Though bovine colostral derived transfer factor was used to develop the formulations of this invention, it is well known to anyone skilled in the art that other kinds and sources of transfer factor could be used.

Table 2, shows a breakdown of a formulation of transfer factor nutraceuticals and carriers for treating Cushing syndrome, Cushings disease, adenomas, onchocerciasis, hypothyroidism or EPM. In Table 2 and all the other tables references to "lb" (pounds) means pounds of body weight.

Columns 2, 3 and 4 of Tables 2–6 show the approximate high, low and preferred amounts, respectively, of the formulation components, in amounts per body weight, to be given to an animal in a single dosage. The formulations in Tables 3 and 4 are very similar to the formulation of Table 2 but they are specialized for dogs and cats respectively. The formulation represented in Table 2 is designed primarily for livestock. The 5 ounces of the formula listed in column 5 is designed to be given to a 1000 pound animal but that will vary and could be given to a 500 pound animal in some cases. The average horse is around 1000 pounds. The 28.3 gm dosage in Table 3 is calculated for a dog weighing about 100–200 pounds but that dosage may also be given to a 15 pound dog. The 2.2 gm formula in Table 4 is for a cat weighing around 15 pounds. However, since these formulas are comprised of nutraceuticals and transfer factor, one skilled in the art will recognize that the ranges are not certain and as critical as the ranges for allopathic drugs.

Further, the formulations in Tables 2–4 are designed to treat mainly chronic diseases, the formulation in Table 5 is designed for mainly acute diseases and the formulation in Table 6 is for both acute and chronic diseases. All the formulations may be given in megadoses to achieve an acute response.

Administration of a formulation of transfer factor, zinc and at least one essential fatty acid will result in at least a partially effective treatment of Cushings syndrome, Cushings disease, adenomas and other benign tumors, onchocerciasis, hypothyroidism or EPM. The treatment is more effective as other nutraceuticals listed in Table 2 are added. The dosage is in milligrams per pound unless otherwise stated. The amounts of the components present in a 5 ounce formulation transfer factor containing the other preferred nutraceuticals is shown in column 5 of Table 2.

Transfer factor at a dosage of about 0.75 mg/lb in combination with about 0.49 mg/lb zinc and 20.57 mg/lb of canola oil, safflower oil or flax oil, sources of essential fatty acids (i.e., 3, 6, 9 omega fatty acids), given once daily to an animal suffering from Cushings syndrome, Cushings disease, adenomas or other benign tumors, onchocerciasis, hypothyroidism or equine protozoal myelytis will result in approximately a 30% to 50% reduction in the size of the benign tumors and/or the symptoms of these listed diseases. All of these components should of course be pharmaceutically acceptable to the animal receiving them.

A combination of Vitamin C at about 2.16 mg/lb and 2.29 mg/lb of yeast in combination with the above listed transfer factor and other fatty acid nutraceuticals will results in approximately a 40% to 50% reduction in the size of benign tumors and/or symptoms of the above listed diseases.

It is preferred in all formulations of the invention that the metal nutraceuticals are proteinated because these forms are easier for the animal to digest and also because the proteinate forms are more stable to pH. The nutraceutical components in the formulations in Tables 2–6 are the active components for treating the various described diseases and syndromes. The fillers and carriers are included to make the formulations more palatable to the animal and also to help preserve the mixture. These include silicon dioxide, maltodextrin, soy and peanut flour, peanut oil, dextrose, whey, spices and flavorings. Mixed tocopherols and choline chloride are nutraceuticals but the effective results described herein can still be achieved by deleting these two components from the formulations.

A daily dosage of 141 mg per pound of body weight of any of the formulations in column 5 of Tables 2, 3 or 4, for 14 days has been successful in treating feline pneumonitis, feline leukemia, feline autoimmune dysfunction, feline flea bit dermatitis, feline hyperthyroidism, feline viral infection, feline ulcerations, feline bacterial infection, canine flea bite dermatitis, canine Cushings disease, malignant tumors, canine autoimmune dysfunctiiion, canine viral and bacterial infection. These treatments for the most part have resulted in complete cures.

Administering a formulation comprising all of the nutraceuticals in Table 2 at the preferred dosage to an animal with benign tumors resulted in about a 60% reduction in the size of the benign tumors and about a 90% reduction in the symptoms exhibited by the animal suffering the above listed diseases and syndromes.

Administration of all of the nutraceuticals in Table 2 at the low dosage in column 3 of those tables results in about a 7% to 100% reduction in the size of the tumors and/or a 30% to 100% reduction in the symptoms exhibited by the animal suffering from those diseases or syndromes.

The stress formulation in Table 5 is also used to treat numerous animal diseases and syndromes and as stated previously, mainly their acute stages. This formulation is also water soluble so it can be given in the animals drinking water. A mixture of about 0.75 mg/lb transfer factor and about 1.42 mg/lb *lactobacillus acidophilus* 109 colony forming units (CFU) given twice daily will result in at least a 30% reduction in clinical symptoms resulting from strangles, dust cough, hypothyroidism and lymphopenia. The same dosage given to young calves will also reduce morbidity by about 30%. The addition of ionic salts or chelates of calcium, magnesium sodium and potassium twice daily in amounts approximating those in column 4 of Table 5 to the above amounts of transfer factor and lactic acid generating bacterial results in a 40% reduction in clinical symptoms of the above mentioned diseases. The addition of about 0.482 mg/lb of citric acid to the above formulation results in about a 45% reduction in the symptoms of the above mentioned diseases. Further addition of Vitamins A, $B_2$, $B_6$, $B_{12}$, C and E, and thiamine results in a 50% reduction in the symptoms of these diseases. The stress formulations given once or twice a day in the dosage presented in column 4 of Table 5 will cure or at least treat and reduce the symptoms of autoimmune dust cough, diarrhea from viral etiology, abscessation, in strangles, snotty nose in strangles, acute viremia in swine, scratches in the horse, hypersensitivity from scratches and onchoceriasis, PURRS, BRD, calf dysentery, coliform infections, *Rhodococcus* infections, *Clostidium* infections, circo virus in birds, and pnemonitis in cats. A combination of transfer factor and lactic acid producing bacteria or this combination further combined with yeast as shown in Table 5 will also treat these diseases but to a lesser extent.

The stress formulation as shown in Table 5 given once or twice daily will also increase the weight gain and feed efficiency of livestock. The weight gain will increase by at least 8%. A combination of transfer factor and lactic acid producing bacteria or this combination further combined with yeast as shown in Table 5 will also increase weight gain but to a lesser extent.

Table 6 shows a breakdown of a performance formulation of transfer factor and nutraceuticals for treating and curing numerous diseases such as arthritis, laminitis, inflammation and malignant tumors. These diseases may also be treated with a combination of transfer factor and super oxide dismutase; transfer factor and glucosamine salts; transfer factor, glucosamine salts and super oxide dismutase; transfer factor, glucosamine salts, super oxide dismutase and glycine; transfer factor, glucosamine salts, super oxide dismutase, glycine and methyl sulfonyl methane; transfer factor, glucosamine salts, super oxide dismutase, glycine, methyl sulfonyl methane and octocosonol or transfer factor, glucosamine salts, super oxide dismutase, glycine, methyl sulfonyl methane, octocosonol and montmorillinite.

TABLE 2

Premix Formulation
(Amounts in mg/lb of body weight unless otherwise stated)

| Component | High | Low | Preferred | Dosage: mg/5 oz. of formula |
|---|---|---|---|---|
| 1-Arginine | 0.5 | 0.005 | 0.05 | 50.00 |
| *Lacto yeast (4.9% of blend) | 69.51 | 0.6951 | 6.91 | 6951.88 |
| Montmorillinite | 1 gm/lb | 0.24118 | 2.4118 | 2411.88 |
| Canola oil (14.5% mix) | 1.5 gm/lb | 2.05 | 20.571 | 20571.88 |
| Safflower oil (14.5% mix) | 1.5 gm/lb | 2.05 | 20.57 | 20571.88 |
| Flax seed oil (55% Alpha Linolenic Acid) (1.0% mix) | 1.5 gm/lb | 2.05 | 20.571 | 1418.75 |
| Phosphorous (Monosodium phosphate) 12% | 15.750 gm | 0.0525 | 5.08 | 5080.00 |
| Calcium carbonate 8.5% (38% calcium) | 13.68 gm | 0.0485 | 4.88 | 4880.00 |
| Methyl sulfonyl methane | 20 | 0.02 | 2 | 2000.00 |
| Transfer factor | 50.00 | 0.05 | 0.75 | 750.00 |
| Vitamin C (ascorbic acid) | 21.62 | 0.2162 | 2.162 | 2162.50 |
| d-Biotin (Vitamin H 2%) | 9.73 | 0.000973 | 0.00973 | 10.00 |
| Vitamin $D_3$ | 29.16 IU | 0.7298 IU | 7.298 IU | 7298.38 IU |
| Vitamin $B_{12}$ | 0.092 | 0.000092 | 0.00092 | 0.92 |
| Folic Acid | 1 | 0.001006 | 0.01006 | 10.06 |
| Niacinimide | 12 | 0.012157 | 0.12157 | 121.57 |
| Pantothenic acid (d-Calcium Pantothenate) 91.6% | 0.324 | 0.0108 | 0.108 | 108.00 |
| Vitamin $B_6$ (Pyridine Hcl 82.3%) | 1.158 | 0.001158 | 0.01158 | 11.58 |
| Vitamin A (Retinol Palmitate) 650 M IU/g feed grade | 600 IU | 4.02 IU | 40.212 IU | 40232.50 IU |
| Vitamin $B_2$ | 0.0554 | 0.002776 | 0.02776 | 27.76 |
| Thiamine (Mononitrate) 83% | 3.09 | 0.00308 | 0.0308 | 30.80 |
| Vitamin E | 72.9 IU | 0.0729 IU | 0.729 IU | 729.42 IU |
| Vitamin K | 1 | 0.0007 | 0.007 | 7.00 |
| Cobalt (Proteinate) 5% | 0.00043 | 0.000043 | 0.00043 | 0.43 |
| Copper (Proteinate) 10% | 0.56 | 0.0112 | 0.112 | 112.00 |
| Iodine (Potassiumiodide) 98% | 0.005 | 0.000053 | 0.00053 | 0.53 |
| Iron (Proteinate) 15% | 3.31 | 0.0331 | 0.331 | 331.16 |
| Magnesium (Oxide) 58% | 10 | 0.04 | 0.4 | 400.00 |
| Manganese (Proeinate) 15% | 1.65 | 0.04 | 0.4 | 332.10 |
| Molybdenum (Sodium Molybdate Dihydrate) 39% | 0.05 | 0.001 | 0.01 | 10.00 |
| Selenium (Sodium Selenite) 44.8% | 0.00162 | 0.000081 | 0.00081 | 1.00 |
| Zinc (Proteinate) 15% | 50 | 0.04987 | 0.4987 | 498.72 |
| 1-Lysine (Mono HCl) | 8.41 | 0.0841 | 0.841 | 841.57 |
| d,1-Methionine | 11.03 | 0.1103 | 1.103 | 1103.86 |
| Mixed Tocopherols | | | | 300.00 |
| Choline Chloride | | | | 2434.00 |
| Sipernat 50 (Silicon dioxide) | | | | 12768.75 |
| Lodex-5 (maltodextrin) | | | | 7519.38 |
| Soy flour (17.5% mix) | | | | 24828.13 |
| Sweet whey | | | | 996.00 |

TABLE 2-continued

Premix Formulation
(Amounts in mg/lb of body weight unless otherwise stated)

| Component | High | Low | Preferred | Dosage: mg/5 oz. of formula |
|---|---|---|---|---|
| BF70 spice | | | | 146.00 |
| Dextrose powder | | | | 750.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 3

Canine Premix Formulation
(Amounts in mg/lb of body weight unless otherwise stated)

| Component | High | Low | Preferred | Dosage: mg/28.37 gm of formula |
|---|---|---|---|---|
| 1-Arginine | 0.5 | 0.005 | 0.05 | 10.00 |
| *Lacto yeast (4.9% of blend) | 69.51 | 0.6951 | 6.91 | 1390.38 |
| Montmorillinite | 1 gm/lb | 0.24118 | 2.4118 | 482.20 |
| Canola oil (14.5% mix) | 1.5 gm/lb | 2.05 | 20.571 | 3887.00 |
| Safflower oil (14.5% mix) | 1.5 gm/lb | 2.05 | 20.57 | 3887.00 |
| Flax seed oil (55% Alpha Linolenic Acid) (1.0% mix) | 1.5 gm/lb | 2.05 | 20.571 | 240.00 |
| Phosphorous (Monosodium phosphate) 12% | 15.750 gm | 0.0525 | 5.08 | 1010.00 |
| Calcium carbonate 8.5% (38% calcium) | 13.68 gm | 0.0485 | 4.88 | 977.00 |
| Methyl sulfonyl methane | 20 | 0.02 | 2 | 400.00 |
| Transfer factor | 50.00 | 0.05 | 2.50 | 500.00 |
| Vitamin C (ascorbic acid) | 21.62 | 0.2162 | 2.162 | 432.50 |
| d-Biotin (Vitamin H 2%) | 9.73 | 0.000973 | 0.00973 | 2.00 |
| Vitamin $D_3$ | 29.16 IU | 0.7298 IU | 7.298 IU | 1459.68 IU |
| Vitamin $B_{12}$ | 0.092 | 0.000092 | 0.00092 | 0.18 |
| Folic Acid | 1 | 0.001006 | 0.01006 | 2.16 |
| Niacinimide | 12 | 0.012157 | 0.12157 | 24.31 |
| Pantothenic acid (d-Calcium Pantothenate) 91.6% | 0.324 | 0.0108 | 0.108 | 21.60 |
| Vitamin $B_6$ (Pyridine Hcl) 82.3%) | 1.158 | 0.001158 | 0.01158 | 2.32 |
| Vitamin A (Retinol Palmitate) 650 M IU/g feed grade | 600 IU | 4.02 IU | 40.212 IU | 8046.50 IU |
| Vitamin $B_2$ | 0.0554 | 0.002776 | 0.02776 | 5.55 |
| Thiamine (Mononitrate) 83% | 3.09 | 0.00308 | 0.0308 | 0.16 |
| Vitamin E | 72.9 IU | 0.0729 IU | 0.729 IU | 145.88 IU |
| Vitamin K | 1 | 0.0007 | 0.007 | 1.40 |
| Cobalt (Proteinate) 5% | 0.00043 | 0.000043 | 0.00043 | 0.086 |
| Copper (Proteinate) 10% | 0.56 | 0.0112 | 0.112 | 22.40 |
| Iodine (Potassiumiodide) 98% | 0.005 | 0.000053 | 0.00053 | 0.106 |
| Iron (Proteinate) 15% | 3.31 | 0.0331 | 0.331 | 66.23 |
| Magnesium (Oxide) 58% | 10 | 0.04 | 0.4 | 80.00 |
| Manganese (Proeinate) 15% | 1.65 | 0.04 | 0.4 | 66.42 |
| Molybdenum (Sodium Molybdate Dihydrate) 39% | 0.05 | 0.001 | 0.01 | 2.00 |
| Selenium (Sodium Selenite) 44.8% | 0.00162 | 0.000081 | 0.00081 | 0.20 |
| Zinc (Proteinate) 15% | 50 | 0.04987 | 0.4987 | 99.74 |
| 1-Lysine (Mono HCl) | 8.41 | 0.0841 | 0.841 | 176.91 |
| d,1-Methionine | 11.03 | 0.1103 | 1.103 | 220.77 |
| Mixed Tocopherols | | | | 60.00 |
| Choline Chloride | | | | 486.80 |
| Sipernat 50 (Silicon dioxide) | | | | 2553.35 |
| Lodex-5 (maltodextrin) | | | | 1508.87 |
| Peanut oil | | | | 496.56 |
| Soy flour (17.5% mix) | | | | 4965.02 |
| Peanut flour | | | | 4965.02 |
| Sweet whey | | | | 400.00 |
| BF70 spice | | | | 29.20 |
| Dextrose powder | | | | 500.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 4

Feline Premix Formulation
(Amounts in mg/lb of body weight unless otherwise stated)

| Component | High | Low | Preferred | Dosage: mg/2.2 gm of formula |
|---|---|---|---|---|
| 1-Arginine | 0.5 | 0.005 | 0.05 | 0.78 |
| *Lacto yeast (4.9% of blend) | 69.51 | 0.6951 | 6.91 | 108.42 |
| Montmorillinite | gm/lb | 0.24118 | 2.4118 | 37.00 |
| Canola oil (14.5% mix) | 1.5 gm/lb | 2.05 | 20.571 | 323.25 |
| Safflower oil (14.5% mix) | 1.5 gm/lb | 2.05 | 20.57 | 323.25 |
| Flax seed oil (55% Alpha Linolenic Acid) (1.0% mix) | 1.5 gm/lb | 2.05 | 20.571 | 22.13 |
| Phosphorous (Monosodium) | 15.750 gm | 0.0525 | 5.08 | 78.70 |
| Calcium carbonate 8.5% (38% calcium) | 13.68 gm | 0.0485 | 4.88 | 75.69 |
| Methyl sulfonyl methane | 20 | 0.02 | 2 | 31.20 |
| Transfer factor | 50.00 | 0.05 | 16.00 | 250.00 |
| Vitamin C (ascorbic acid) | 21.62 | 0.2162 | 2.162 | 33.73 |
| d-Biotin (Vitamin H 2%) | 9.73 | 0.000973 | 0.00973 | 0.156 |
| Vitamin $D_3$ | 29.16 IU | 0.7298 IU | 7.298 IU | 113.90 IU |
| Vitamin $B_{12}$ | 0.092 | 0.000092 | 0.00092 | 0.014 |
| Folic Acid | 1 | 0.001006 | 0.01006 | 0.168 |
| Niacinimide | 12 | 0.012157 | 0.12157 | 1.90 |
| Pantothenic acid (d-Calcium Pantothenate) 91.6% | 0.324 | 0.0108 | 0.108 | 1.68 |
| Vitamin $B_6$ (Pyridine Hcl) 82.3% | 1.158 | 0.001158 | 0.01158 | 0.18 |
| Vitamin A (Retinol Palmitate) 650 M IU/g feed grade | 600 IU | 4.02 IU | 40.212 IU | 627.60 IU |
| Vitamin $B_2$ | 0.0554 | 0.002776 | 0.02776 | 0.43 |
| Thiamine (Mononitrate) 83% | 3.09 | 0.00308 | 0.0308 | 0.48 |
| Vitamin E | 72.9 IU | 0.0729 IU | 0.729 IU | 11.38 IU |
| Vitamin K | 1 | 0.0007 | 0.007 | 0.11 |
| Cobalt (Proteinate) 5% | 0.00043 | 0.000043 | 0.00043 | 0.006 |
| Copper (Proteinate) 10% | 0.56 | 0.0112 | 0.112 | 1.75 |
| Iodine (Potassiumiodide) 98% | 0.005 | 0.000053 | 0.00053 | 0.008 |
| Iron (Proteinate) 15% | 3.31 | 0.0331 | 0.331 | 5.17 |
| Magnesium (Oxide) 58% | 10 | 0.04 | 0.4 | 6.24 |
| Manganese (Proeinate) 15% | 1.65 | 0.04 | 0.4 | 5.18 |
| Molybdenum (Sodium Molybdate Dihydrate) 39% | 0.05 | 0.001 | 0.01 | 0.156 |
| Selenium (Sodium Selenite) 44.8% | 0.00162 | 0.000081 | 0.00081 | 0.156 |
| Zinc (Proteinate) 15% | 50 | 0.04987 | 0.4987 | 7.78 |
| 1-Lysine (Mono HCl) | 8.41 | 0.0841 | 0.841 | 13.80 |
| d,1-Methionine | 11.03 | 0.1103 | 1.103 | 17.22 |
| Mixed Tocopherols |  |  |  | 4.68 |
| Choline Chloride |  |  |  | 38.0 |
| Sipernat 50 (Silicon dioxide) |  |  |  | 199.06 |
| Lodex-5 (maltodextrin) |  |  |  | 117.30 |
| Sweet whey |  |  |  | 155.37 |
| BF70 spice |  |  |  | 2.28 |
| Dextrose powder |  |  |  | 250.00 |
| Glucosamine HCl |  |  |  | 100.00 |
| Pernaconniculus-Chondroitin |  |  |  | 200.00 |

*Lactic acid generating bacteria is two-thirds of component and yeast is one-third; lactic acid generating bacteria is 500,000,000 CFU/gm, yeast (e.g., "Saccharamyces") 250,000,000 CFU/gm

TABLE 5

Stress Formula
(Amounts in mg/lb of body weight unless otherwise stated)

| Component | High | Low | Preferred | Dosage: mg/ounce of formula |
|---|---|---|---|---|
| Calcium Pantothenate | 1.80 | 0.09 | 0.028 | 28.00 |
| Vitamin C (ascorbic acid) | 20.00 | 0.056 | 0.017 | 17.00 |
| Vitamin $B_{12}$ | 13.00 | 0.13 | 0.198 | 198.59 |
| Vitamin A | 600.00 IU | 0.10 IU | 0.014 | 14.00 |
| Vitamin $B_2$ | 1.20 | 0.065 | 0.018 | 18.00 |
| Thiamine | 16.00 | 0.0308 | 0.017 | 17.00 |
| Vitamin E | 72.9 IU | 0.729 IU | 0.012 | 12.48 |
| Magnesium Sulfate | 10.00 | 0.113 | 0.113 | 113.00 |

TABLE 5-continued

Stress Formula
(Amounts in mg/lb of body weight unless otherwise stated)

| Component | High | Low | Preferred | Dosage: mg/ounce of formula |
|---|---|---|---|---|
| *Lactobacillus acidophilus | 10.00 | 0.467 | 1.418 | 1418.00 |
| Sodium Chloride | 166.00 | 0.236 | 2.368 | 2368.00 |
| Dipotassium phosphate | 116.00 | 5.85 | 1.773 | 1773.00 |
| Citric acid | 31.00 | 1.59 | 0.482 | 482.00 |
| Yeast (hydrolyzed) | 180.00 | 0.1957 | 0.283 | 283.00 |
| Glycine | 0.142 | 0.0142 | 0.142 | 141.80 |
| Potassium chloride | 18.00 | 0.93 | 0.283 | 283.00 |
| Vitamin $D_3$ | 29.00 | 0.729 | 0.002 | 1.56 |
| Dextrose | 40.00 | 2.00 | 21.38 | 21375.00 |
| Artificial flavor | 0.028 | 0.0028 | 28.548 | 28.30 |
| Transfer Factor | 50.00 | 0.05 | 0.75 | 750.00 |
| Sipernat (silicon dioxide) | | | 0.05 | 56.70 |

*$10^9$ colony forming units (CFU)/gm

TABLE 6

Performance Formula
(Amounts in mg/lb of body weight unless otherwise stated)

| Component | High* | Low* | Average* | Dosage: mg/oz. of formula |
|---|---|---|---|---|
| Super oxide dismutase | 60.0 | 0.6 | 6.0 | 6000.0 |
| Glucosamine salts | 65.0 | 0.65 | 6.5 | 6500.0 |
| Transfer factor[1] (horses, cows) | 15.0 | 0.15 | 1.5 | 1500.0 |
| Transfer factor[1] (goats) | 10.0 | 0.10 | 1.0 | 3000.0 |
| Transfer factor[1] (dogs, cats) | 50.0 | 0.5 | 5.0 | 14000.0 |
| Pernaconniculus-Chondro-itin (mucopolysaccharides) | 16.5 | 0.165 | 1.65 | 1650.0 |
| Boswellic acids | 30 | 0.3 | 3.0 | 3000.0 |
| Di-methyl glycine | 27.0 | 0.27 | 2.7 | 2700.0 |
| Methyl sulfonyl methane | 27.0 | 0.27 | 2.7 | 2700.0 |
| Octocosonol | 2.0 | 0.004 | 0.04 | 400.0 |
| Montmorillinite | 30.0 | 0.3 | 3.0 | 3000.0 |

*These amounts are calculated for livestock animals weighing about 450 to 1,000 pounds, goats weighing about 150 pounds, and dogs and cats weighing from about 8 to about 15 pounds.
[1]The amount of transfer factor may vary for different species but the amounts for the other components remain the same for each species.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All patents, patent applications, publications, and references cited herein are expressly incorporated by reference in their entirety.

EXAMPLE 1

A seven year old warm blooded Pajarro horse was urinating frequently and showing other clinical signs of pre Cushings syndrome. Morning and evening thyroid readings of 22.33 ng and 19.8 ng and insulin readings of 31.0 UIU and 43.2 UIU respectively confirmed this diagnosis. The horse was place on a daily dose of 5 ounces of the premix formulation as shown in column 5, Table 2. After seven days on the formulation the frequency of urination had greatly decreased and the horse's temperament had significantly improved. Blood studies taken 32 days after the initiation of treatment, which showed morning and evening thyroid readings of 28.4 ng and 42.7 ng and insulin readings of 40.3.0 UIU and 33.62 UIU, respectively, exhibited an improved thyroid level and cortisol rhythm.

EXAMPLE 2

Two horses, one 7 years old and the other a yearling, exhibited signs of chronic dust cough, a condition that has an allergic component with increased eosinophilia. The 5 year old thoroughbred had been treated with tribrissin and an antihistamine. His intake eosinophil count was 8 and the monocyte count was 7. After being placed on 1 ounce of the stress formulation as shown in column 5, Table 5, twice daily for 14 days, the horse appeared to be in complete remission. He was then placed on a treatment of 5 ounces daily of the premix formulation as shown in column 5, Table 2. At the end of 22 days, the cough was completely eliminated and the eosinophil count was down to 3 and the monocyte count was down to 6. The yearling who had been on expensive antibiotics and cough suppressants showed no clinical symptoms of the chronic cough after receiving a daily dose of 5 ounces of the premix formulation as shown in column 5, Table 2, for 10 days.

EXAMPLE 3

Two horses were received that had been positively diagnosed with Cushings disease and had previously been treated with Pergolyde and Cyprohexadine. One of the horses had initial morning and evening thyroid readings of 5.3 ng and 7.4 ng and insulin readings of 142.8UIU and 110.2UIU, respectively. Both horses showed dramatic improvement after 10 days on a daily 5 ounce dosage of the premix formulation as shown in column 5, Table 2. Both horses continued with a positive response after being maintained for 2 months on the same dosage. Morning and evening blood results of thyroid readings of 7.0 ng and 16.1 ng and insulin readings of 110.3UIU and 65.2UIU confirmed improvements in thyroid function and cortisol rhythm.

EXAMPLE 4

The stress formulation (Table 5) was used successfully to treat two thoroughbred racehorses with chronic dust cough. After 5 days of receiving two ounces per day of the stress formulation shown in column 5, Table 5, both horses had dramatically improved with one horse no longer showing any symptoms of the eosinophilic dust cough and the other horse showing approximately a 60% improvement over its previous symptoms.

EXAMPLE 5

Three pigs with acute viral infection and temperatures of 105° were placed on one ounce daily of the stress formulation shown in column 5, Table 5. Within 24 hours, all three pigs ate normally and exhibited normal temperatures.

EXAMPLE 6

Two foals, 10 and 12 days old, suffering from diarrhea had not responded to previous treatments of antibiotics and electrolytes. Both foals were placed on one ounce of the stress formulation as shown in column 5, Table 5, twice daily. After two days on this treatment, both foals were symptom free.

EXAMPLE 7

An 80 pound golden retreiver that has reoccurring squamous cell carcinoma was given 28 grams of the canine formula as shown in column 5, Table 2, per day for 6 weeks. The 6-week administration of this formulation per day showed a 40% reduction in the tumor.

EXAMPLE 8

Five cats were suffering from upper respiratory infections. They were treated with a dosage of the stress formulation in milligrams per pound as shown in column 4, Table 5. All cats responded with remission of symptoms in three days after initiation of this treatment.

EXAMPLE 9

A 16 year old gelding, Dutch warm blood was exhibiting no energy, irritability, awkward movement, a chronic girth itch and was unable to carry his head correctly. A blood test showed a low lymphocyte count of 624/uL, with 1500 to 7700/uL being normal, and also showed a marginally low T4 thyroid count of 1.0 ug/dL. He had been receiving long term treatments of Trimethoprim Sulfur, vitamins and some nutritional changes. This treatment was stopped and he was administered orally 1 oz of the stress formulation twice daily as shown in column 5 of Table 5 for a few days and showed some improvement. He was then placed on a daily oral dose of 5 oz of the premix formulation as shown in column 5 of Table 2. After 5 days of treatment the horse was significantly improved, eating better and holding his head erect. A blood test taken seven days after the premix formulation treatment began showed that the lymphocyte count had increased to 940/uL. Approximately 35 days after treatment with the premix formulation, another blood test showed a lymphocyte count improvement to 1404/uL and a thyroid increase to 1.5 ug/dL. A normal thyroid range is 0.9 ug/dL to 2.8 ug/dL. His clinical appearance was excellent, locomotion had improved, cervical balance was better and the girth itch appeared 80 percent improved. He has remained well and is being used as a normal performance horse in three-day eventing.

EXAMPLE 10

A seven year old mustang gelding with a three year duration of onchocerciasis exhibiting stomach ulceration and severe pruritus of tail and main, had been treated with conventional cortisone and antibiotics with little success. The horse was placed on a daily oral treatment of 5 oz. of the premix formulation as shown in column 5 of Table 3. After two months a blood test showed that the white blood cell counts had stabilized. After six months the thyroid level was normal, the clinical symptoms had gone and the horse was in complete remission.

EXAMPLE 11

Approximately 60 young foals were suffering from severe cases of strangles also known as *Strep Equi*, a secondary infection of *Rhodococcus equi* and upper respiratory infections. The problem was being complicated by heat causing dehydration and also by dust. Most of the foals were also suffering from dust pneumonia. The foals had not responded to previous conventional therapy of antibiotics, of gentomycin sulfate, penicillin, amikacin. Twenty-one of the foals were first treated with one ounce of the stress formulation shown in column 5, Table 5, twice a day for two days and then were treated with one ounce once a day for three more days. Three foals showed significant recovery after five days. These three foals were treated with one ounce of the stress formulation described above twice a day and no antibiotics. Two of the foals that had just contracted the disease responded immediately in 48 hours showing very little coughing, clear nostrils and increased appetite. The other foal had to be placed on antibiotics in addition to the stress formulation and responded in five days with supportive antibiotics. The remaining 18 diseased foals with strangles and upper respiratory ailments received one ounce twice daily of the stress formulation in column 5, Table 5 for two days and then received one ounce daily of the same stress formulation for the next 8 days. Blood tests were initially taken on these foals and again ten days after treatment began.

About 14 of these remaining foals showed a marked improvement after 10 days with no antibiotics. The initial blood results show elevated neutrophil and monocyte counts on the majority of the foals with high band cell counts. Foals with early signs of the strep equi infection showed depressed lymphocyte counts. After ten days of treatment blood results showed normalization of the differential of neutrophils, lymphocytes, and monocytes. The most significant finding was total reduction of band cells in all but one foal. Platelet cells were increased in practically all foals.

Reduction of band cells is indicative of a powerful immune response. The platelet cell increase may be from stimulation of stem cells. Hydration improved from the electrolyte and probiotic combination with transfer factor. Also, as an adjunct to antibiotic therapy, the stress formula appeared very beneficial and in early onset of disease the stress formula appeared to boost the immune response to the extent that antibiotic therapy may not be necessary.

The problem with treating strangles with antibiotics is that for some reason antibiotics allow the "*Strep equi*" organism to lie dormant causing a disease of bastard strangles later in life in that lymph nodes containing the bacteria can show up at any age and create a chronic illness or acute death.

EXAMPLE 12

This case involved dairy drop calves. These calves usually receive very little colostrum if any and, upon arrival at the farm, frequently break with shipping fever symptoms, the term used for generalized viral infections, upon arrival at the farm. These symptoms usually last ten days with conventional antibiotic therapy and result in a high mortality rate. However, the disease also often leaves permanent scarring of the lungs and gastrointestinal tract which leaves poor producing dairy cows. Ten of the calves received one ounce daily of the stress formulation as set forth in column 5, Table 5, for four days and then one half ounce of that formulation for the next three days. The ten controls received no stress formulation. After 7 days, one of the stress formulation treated calves contracted shipping fever and had to be treated with antibiotics. Out of the 10 controls, 7 calves had to be treated with antibiotics. The overall test showed a 60 to 80 percent reduction in morbidity.

EXAMPLE 13

A 10 year old 70 pound golden retriever suffering with a squamous papilloma of the eyelid of a clinical size of about 1cm in length, received surgery to remove the tumor. Within two months the tumor had reoccurred and had grown rapid rapidly again to 1 cm. The retriever was placed on a daily dosage of 28 grams of the canine formula as shown in column 5, Table 3. After 60 days on this dosage of the canine formula, not only had the tumor stopped growing but the size of the tumor was reduced by 30%.

EXAMPLE 14

A 1000 pound horse was suffering from scratches. Scratches is a bacterial, fungal infection of the rear legs consisting of *staphilococcus* and *Trichophyton mentagreophytes*. After 7 days of receiving 1 ounce twice daily of the stress formulation as shown in column 5, Table 5, the infection on the rear legs had improved at least 50% and the swelling and sores that had occurred were greatly reduced.

EXAMPLE 15

A nine year old thoroughbred cross, gelding, performance horse exhibited clinical signs of Cushing's syndrome, including heavy breathing, ulcers around the coronet band and hypothyroidism. He had previously been treated with Azium, Ventipulium, prednisone and broncodilators but showed no improvement. A daily treatment of approximately 5 oz. of the premix formulation as set forth in column 5 of Table 2 showed some improvement. After the addition of 750 mg of transfer factor to the above Premix dosage, all given daily, the horse showed immediate and significant improvement in it's performance. The horse continued to improve and after being kept on the same transfer factor and premix formulation, the horse recovered completely. When the horse was taken off the transfer factor and premix, he relapsed but recovered after being placed again on the same transfer factor and premix formulation again.

EXAMPLE 16

A 1,000-pound gelding suffering from onchoceriasis as exhibited by skin thickness and other symptoms is administered 750 mg of transfer factor, 500 mg of total zinc and 2 gm of flax seed oil. The onchoceriasis symptoms are reduced as exhibited by a 60% reduction in skin thickness.

EXAMPLE 17

A 1000 pound horse with a temperature of 103° F. is given 750 mg of transfer factor, 500 mg of total zinc, 2 gm of Flax seed oil, 7 gm of hydrolyzed yeast and 1.5 gm of Vitamin C. The horse shows a reduced temperature of approximately 100.5° F. within 48 hours.

EXAMPLE 18

A 1000 pound gelding exhibiting a low lymphocyte count is given a daily dosage of 750 mg of transfer factor, 500 mg of total zinc, 2 gm of Flax seed oil, 7 gm of hydrolyzed yeast, 1.5 gm of Vitamin C, 2 gm of methyl sulfonyl methane, 15 mg of arginine and 1103.86 mg of methionine. After being given this dosage for 30 days, the lymphocyte count of the gelding is increased 30%.

EXAMPLE 19

A colt weighing 1000 pounds with a bacterial infection with a minor cut on the leg and a temperature of 105° is given 750 mg of transfer factor and 2.35 gm of *lactobacillus acidophilus*. With 48 hours after administration of this composition, the temperature is reduced to 101° F. and the swelling is reduced approximately 50%.

EXAMPLE 20

A 3-year old 1000 pound colt having a respiratory infection that is viral in origin with a temperature of 104° responds to 750 mg of transfer factor, 2.3 gm of *lactobacillus acidophilus*, 500 mg of zinc and 3 gm of yeast given daily by showing a reduction in temperature to approximately 101.50° F. and improved breathing within 72 hours following the initiation of this treatment.

EXAMPLE 21

A 1000 pound horse with hoof separation from white line disease and micro absecessation responds to a daily dosage of 750 mg of transfer factor, 2.3 gm of *lactobacillus acidophilus*, 500 mg of total zinc, 3 gm of yeast and 24.12 gm of montmorillinite. After 90 days of treatment the horse shows improved hoof growth of approximately 1 cm and approximately a 60% reduction of white line disease or absecessation.

EXAMPLE 22

A 1000 pound gelding with Cushings disease is fed 5 ounces daily of the premix formulation shown in column 5, Table 2, except that the horse receives 3 gm of Flax seed oil and no canola oil or safflower oil. With 30 days of continuous treatment at this dosage, the clinical symptoms of frequent urination, low blood sugar and low alertness are improved approximately 30%. With 90 days at this treatment, the Cushings symptoms are 50% reduced.

EXAMPLE 23

A 15-pound cat with flea bite dermatitis is treated with 250 mg of transfer factor, 108 gm of *lactobacillus acidophilus* for 10 days and showed a 40% improvement in arithmic ulcerations of the skin caused by the flea bites.

EXAMPLE 24

A 15 pound cat with reddened skin under the stomach and partial hair loss from flea bite dermatitis and possibility autoimmune or atopic dermatitis is treated daily with 250 mg of transfer factor, 37 mg of lactic acid bacteria, 72 mg of hydrolyzed yeast, 7.78 mg of zinc and 37.6 mg of montmorillinite for 10 days. The clinical symptoms of reddened skin and hair loss at the end of this time are reduced approximately 50%.

EXAMPLE 25

A 15 pound cat tests positive to feline leukemia virus. With 60 days treatment of a daily dose of 250 mg of transfer factor, 37 mg of *lactobacillus acidophilus*, 7.78 mg of zinc and 72 mg of hydrolyzed yeast, the cat is no longer exhibiting clinical symptoms of feline leukemia virus and the laboratory tests are negative.

EXAMPLE 26

A 15 pound cat with flea bite dermatitis is treated daily with 250 mg of transfer factor, 37 mg of *lactobacillus acidophilus*, 72 mg of hydrolyzed yeast and 37.6 mg of montmorillinite. Within 7 days of daily treatment, the ulcerations occurring from the flea bite dermatitis are at least 40% reduced.

EXAMPLE 27

One day old drop dairy calves weighing 100 pounds each with shipping fever exhibiting clinical symptoms of poor appetite, diarrhea and an elevated fever are administered a daily dosage in their food of 375 mg of transfer factor, 709 mg of *lactobacillus acidophilus*, 14 mg of calcium pantothenate, 56.5 mg of a chelated magnesium, 1158 mg of a sodium salt, 141 mg of a potassium salt and 881 mg of a phosphate. Within 4 days of receiving this treatment, the morbidity rate in the calves is reduced 50% as compared to controls.

EXAMPLE 28

Ten pigs each weighing 10 pounds and exhibiting elevated temperatures and slightly loose stool are administered 250 mg of transfer factor, 467 mg of *lactobacillus acidophilus*, 9.24 mg of calcium pantothenate, 37 mg of magnesium, 781 mg of a sodium salt, 93 mg of a potassium salt and 585 mg of phosphorus in the form of dipotassium phosphate along with 15 mg of citric acid daily. These pigs exhibit a 50% reduction in morbidity within 5 days of administration of this formulation in comparison to controls that do not receive the formulation.

EXAMPLE 29

Ten show chickens weighing 10 pounds each show signs of elevated temperature, distress from shipping fever complex that is viral in origin, poor appetite and lethargy. A daily dosage of 250 mg of transfer factor, 467 mg of *lactobacillus acidophilus*, 924 mg of a chelated calcium pantothenate, 37 mg of a magnesium sulfate, 781 mg of a sodium salt, 93 mg of a potassium salt, 585 mg of dipotassium phosphate, 159 mg of citric acid, 4.62 mg Vitamin A, 5.4 mg Vitamin $B_2$, 65.3 mg Vitamin $B_{12}$, 5.8 mg Vitamin C and 4.1 mg Vitamin E daily in their drinking water reduces morbidity 50% within 72 hours as compared to a control group that does not receive this treatment.

EXAMPLE 30

Five horses weighing approximately 500 pounds each with Strangles as exhibited by snotty noses, elevated temperatures and swollen lymph nodes are administered 750 mg of transfer factor, 1.42 gm of *lactobacillus acidophilus*, 28 mg of calcium pantothenate, 113 mg of magnesium sulfate, 2368 mg of sodium chloride, 283 mg of potassium chloride, 1773 mg of dipotassium phosphate, 482 mg of citric acid along with 14 mg Vitamin A, 18 mg Vitamin $B_2$, 17 mg Thiamine, 1,56 mg Vitamin $D_3$, 17 mg Vitamin C and 12.48 mg Vitamin E, twice daily. The morbidity rate for these horses is reduced 50% as shown by a 50% reduction in symptoms when compared to a control group not receiving the above formulation. Chronic abscessation is eliminated approximately 40% again when compared to a control group not receiving the above formulation.

EXAMPLE 31

A 1000 pound horse with a flat sarcoid in the ear tip is given 5 ounces of the premix formulation as shown in column 5 of Table 2 daily for 60 says. At the end of the 60-day treatment, the sarcoid is reduced 30% in size.

EXAMPLE 32

A serious outbreak of mycoplasma occurs in 20 goats exhibiting symptoms of ocular and nasal discharge. The milking goats are also suffering mastitis as a result of the disease. The goats are given 1 ounce daily of the stress pak formulation shown in column 5, Table 4, for 7 days. A 40% improvement in the clinical symptoms of the mycoplasma is seen with administration of this stress dosage.

EXAMPLE 33

A 1000 pound warmblooded horse having equine protozoal myelitis is treated daily for four weeks with 5 ounces of the premix formula as shown in column 5, Table 2, in addition to traditional medication such as pyrimethamine and sulfadiazine. This treatment produces a 50% improvement in symptoms.

EXAMPLE 34

A 1000 pound Arabian horse having a one inch melanoma situated below the tail head and growing at ½ inch per 6 months is treated for 60 days with 5 ounces daily of the premix formulation as shown in column 5, Table 2. This treatment stops the growth of the melanoma and reduces the size of the tumor about 20%.

EXAMPLE 35

Group I

Two hundred forty crossbred heifers are randomly divided into three groups of 80 calves each. They are processed within 12 hours after arrival, individually weighed and receive a combination modified-live virus vaccine consisting of infectious bovine rhinotracheitis (IBR) virus, killed bovine viral diarrhea virus (BVD), modified-live bovine respiratory syncytial virus (BRSV) and killed parainfluenza-3 (PI3) virus, a multivalent bacterin-toxoid against 7 clostridial species; a dormectin dewormer (Ivomec); and a progesterone implant. Ten days following processing, the calves are given a booster with the same modified-live vaccine they received initially. One set of 80 calves averaging 440.1 pounds receive a 1 ounce dose of the stress formula, as set forth in column 5, Table 5, dissolved in 1 ounce water via dosesyringe at the time of processing. Thereafter, they are given doses of 1 ounce of stress formula daily mixed in the feed (total mixed ration—TMR) for four days after processing. A second set of 80 calves averaging 440 pounds receive 1.5 ml/cwt of tilmicosin (Micotil) at the time of initial processing. The third set of 80 averaging 449.9 pounds serves as controls. The sets are observed for 26 days after processing at which time each of the calves is again weighed and feed efficiency calculated collectively for each group.

Group II

Two hundred crossbred stocker heifers are randomly divided into four groups of 50 calves each. They are processed in the same manner as the stocks in Group I. One set of 50 calves averaging 441 pounds receives 1 ounce of the stress formula as set forth in column 5, Table 4, per day in their TMR for five days. A second set of 50 calves averaging 433 pounds receive ½ ounce of the same stress formula in their TMR for five days. A third set of 50 calves averaging 447 pounds receive a metaphylactic 1.5 ml of tilmicosin per cwt at the time of initial processing. The fourth set of 50 calves averaging 432 pounds serve as controls. Each heifer in all four sets receives the modified live virus combination of IBR, PI3, BVD and BSV vaccine booster ten days following initial processing. The groups are observed for 30 days after processing at which time each of the calves are again weighed and feed efficiency is calculated collectively for each group.

Statistics:

Statistical analysis of weight gain: A one-way analysis of variance is done with classification: treatment of animals in treatment. F-tests and LSD mean separation was done using alpha=0.05 as type I error rate. Software is SAS (1999), procedure GLM.

Statistical analysis of BRD morbidity: Chi-square analysis utilizing Fisher's exact test with a 0.05 or less probability interpreted as significant is used to interpret the differences in morbidity rates between groups.

Results

The results are listed in Tables A and B below.

For Group I, there were no sick pulls from the eighty head of heifers that were treated with 1 ounce of stress formula in 1 ounce of water solution via dosesyringe the day of processing and 1 ounce of stress formula per day added to the TMR for the four days following processing. There were 17 sick pulls and 4 repulls for BRD from the control group while there were 12 sick pulls and 1 repull from the tilmicosin set.

The heifers in the Group I stress formula set had an average daily gain of 3.63 pounds for the 26 day test period, which is statistically significant when compared to the other two sets. The average daily weight gain (ADG) of the tilmicosin and control sets was 2.96 and 3.08 pounds respectively. Feed efficiency for the stress formula, tilmicosin and control sets was 6.73, 6.94 and 6.66, respectively.

The heifers in the 1 ounce stress formula dosage set in Group II have an average daily gain of 3.2 pounds and those in the one half ounce stress formula dosage set have an average daily gain of 3.05 pounds. The tilmicosin and control sets have an average daily gain of 2.88 pounds and 2.92 pounds, respectively. The feed efficiency for the 1 ounce stress formula is 5.31 while the values for the half ounce stress formula, the tilmicosin and the control sets are 6.09, 6.10 and 5.99. respectively.

There were 11 sick pulls and repulls for treatment of BRD in the set of fifty heifers receiving 1 ounce of stress formula per day added to the total mixed ration for five days, beginning on the day of processing while there were 13 sick pulls and 4 repulls for BRD treatment in the group receiving ½ ounce TF in their TMR for five days. There were 5 sick pulls and 2 repulls from the tilmicosin set during the 30 day test period. Eleven BRD sick pulls and 2 repulls occurred in the control set of heifers.

Discussion:

Upon comparing the differences in the sick pull rate between the sets in Group I, the stress formula appeared to provide significant protection from BRD during the 26 day testing period. Stress formula also significantly increased the average daily gain.

In Group II, the heifers in both sets achieved better weight gain than those in the other two sets. However, in Group II the protection from BRD appears to be less than that of tilmicosin. When one compares the effect of TF on BRD between Group I and Group II, the results appear to be inconsistent until it is realized that the heifers in Group II did not receive their initial dose of stress formula via dosesyringe during the processing. This evidence is a strong argument for administration of the initial dose via dosesyringe or capsule to assure that every subject receives at least the entire first dose instead of relying totally on receiving the stress formula via the TMR. The heifers that were pulled for treatment in the two stress formula sets may not have eaten a full portion of the TMR on the first critical, stressful day and therefore did not receive enough stress formula to stimulate the immune system.

When comparing the heifers receiving the full ounce per day stress formula with the set receiving a half ounce per day, there is not significant differences in the performance of the heifers. It is very possible that if both dosages are administered initially via dosesyringe or capsule the differences may be even less.

It should be noted here that the value of the weight gained by the stress formula sets in excess of the weight gained by the other sets in Group II was more than enough to compensate for the cost of treatments for BRD in the stress formula sets.

In high risk cattle that are not preconditioned such as the heifers in these studies, direct stimulation of the immune system with stress formula along with vaccine administration appeared to indeed enhance the level of immunity against BRD. Stress formula appeared to decrease the need for antibiotic treatment and or enhance the effectiveness of antibiotic therapy.

TABLE A

Results for Group I
1 oz. stress formula daily - drenching the first day followed by 4 days of top dressing

| Treatment Group | # of heifers | ADG | Kg (lbs) | Pulls | Repulls | Feed Efficiency | Sick pulls |
|---|---|---|---|---|---|---|---|
| Stress Formula (1 oz/day) | 80 | 3.63 | 200.0 (440.1) | 0 | 0 | 6.73 | 1.65 |
| Tilmicosin (Micotil 1.5 ml/cwt) | 80 | 2.96 | 200.0 (440.0) | 12 | 1 | 6.94 | 1.35 |
| Control | 80 | 3.08 | 204.5 (449.9) | 17 | 4 | 6.66 | 1.40 |

TABLE B

Results for Group II
Stress Formula daily - 5 days of top dressing only

| Treatment Group | # of heifers | ADG | Kg (lbs) | Pulls | Repulls | Feed Efficiency | Sick pulls |
|---|---|---|---|---|---|---|---|
| Stress Formula (1 oz/day) | 50 | 3.20 | 200.5 (441.0) | 11 | 4 | 5.31 | 1.45 |
| Stress Formula (1/2 oz/day) | 50 | 3.05 | 198.8 (433.0) | 13 | 4 | 6.09 | 1.39 |
| Tilmicosin (Micotil 1.5 ml/cwt) | 50 | 2.88 | 203.2 (447.0) | 5 | 2 | 6.10 | 1.31 |
| Control | 50 | 2.92 | 196.4 (432.0) | 11 | 2 | 5.99 | 1.33 |

EXAMPLE 36

A 22-year-old thoroughbred with osteomylitis and chronic laminitis of approximately 1,000 pounds was placed on one-ounce daily of the performance formula as shown in column 5, Table 6 (horses) for six months. He was also suffering from leaky bowel syndrome as a result of having received 3 gm of butazolidin twice a day over a period of time and had a hemoglobin of 10.9 g/dl. Upon initiation of the performance formula, treatment with butazolidin was stopped. After two months on the performance formula the hemoglobin rose to 14 g/dl showing the elimination of leaky bowel syndrome. After the six months on the performance formula the horse exhibited an 80% reduction in osteomylitis and laminitis symptoms.

EXAMPLE 37

An approximately 1,000 pound, 20 year old Arabian mare was suffering from fertility problems and chronic laminitis. The only way the horse was able to stand was by administration of 500 mg of Banamine twice a day. This NSAID interfers with fertility. The horse was placed on one-ounce daily of the performance formula as shown in column 5, Table 6 (horses) for 30 months and the Banamine was slowly tapered off upon initiation of this treatment and was completely stopped after a few weeks. At the end of 3 months there was an 80% improvement in the laminitis. After 30 months, the laminitis was still 80% improved and the chances of conception in this mare were enhanced.

EXAMPLE 38

Splenectomies were performed on two dogs diagnosed with hemangiosarcomas of the spleen and the dogs were given six weeks to live. The first dog, a 12 years old Australian shepherd weighing 40 pounds that had been receiving cortisone at one mg per pound and the pain reliever Rymadal 500 mg bid, was placed on three grams of the performance formula as shown in column 5, Table 6 (for dogs). Treatment of cortisone and Rymadal was immediately stopped upon initiation of the performance formula. The dog lived an additional 12 months. The second dog, a nine year old Airdale had been on Etogesic 500 mg daily and prednisone of twenty mg bid. The dog was placed on three grams of the performance formula (dogs) as shown in column 5, Table 6 and treatment with Etogesic and prednisone was tapered off. After one year and three months on the performance formula, ultrasound tests and radiographic and blood chemistries showed no signs of hemangiosarcoma and no pain relievers or prednisone were being administered.

EXAMPLE 39

A nine year old golden retriever was diagnosed with extra skeletal osteosaarcoma with a poor prognosis of several weeks to live. After being placed on three grams of the performance formula as shown in column 5, Table 6 (dogs) for six months, the dog was in total remission and had been taken off all pain relievers.

EXAMPLE 40

Three goats with carpal joint arthritis that were non responsive to Banamine and/or Butazolidine of one gram daily were placed on three grams of the performance formula as shown in column 5, Table 6 (i.e 1000 mg/oz. of transfer factor). The Banamine and Butazolidine were completely halted upon initiation of the performance formula treatment. After six months on the performance formula treatment all three animals showed an approximately 80% improvement as exhibited by reduction in swelling and increased mobility. This 80% improvement rate has continued for 6 months.

EXAMPLE 41

A 12 year old male Lhasa Apso was diagnosed as having acute arthritis and a deformed right front leg at the age of 10 years. The dog barely moved all day, was unable to jump onto or off of furniture, and when he did walk, it was very slowly and with a very pronounced limp. For one and one-half years the dog was treated with prednisone (5 mg) every 1–2 days and Glycoflex® every day. At the end of that time, the leg muscles had atrophied and very serious arthritis symptoms remained. It was a two-hour task to get the dog to eat each night. He was then placed on three grams of the performance formula as shown in column 5, Table 6 (dogs) mixed with his dinner each night. Within four weeks he had lost four pounds (down to 19 from 23) and had become as active as a puppy, jumping on/off furniture, running up/down stairs and on walks, chasing squirrels in the backyard and barking at anything that moved. The limp was only visible upon first getting up after lying down for long periods of time. Otherwise, the animal moved too fast for it to be noticeable. The dog had regained his appetite, emptying his bowl at every feeding, and his coat now had a shine to it. The dog has been on the performance formula for one year and is also on prednisone (2.5 mg every third day) and Glycoflex® and, except for the very slight limp mentioned above, exhibits excellent health.

EXAMPLE 42

Feline pneumonitis is reduced dramatically by giving stress formula orally at a rate of 5.1 gms per cup of water to infected cats. At different times, in excess of twenty cases of young kittens suffering from feline pneumonitis that were not responding to a daily dosage of five mg of clavamox per pound of body weight were given 3 gm in one cup of water of the stress formula daily as shown in column 5, Table 5. Treatment with clavamox was halted upon initiation of the stress formula treatment. After five days on the above stress formula protocol all of these kittens appeared symptom free of the pneumonitis.

EXAMPLE 43

A herd of cattle in Fort Bidwell, Calif. had a chronic problem with calf dysentery with a death rate of 63% and morbidity of 90%. This problem had persisted for seven years. Treatments that resulted in no improvement included the antibiotics tetracycline, mycotil, sulfur and penicillium along with the other traditional treatments such as fluids and anti-diarrheal medications like kaopectate. The University of Califronia, Davis, and the University of Washington were unable to provide a solution. Forty test calves weighing around 100 pounds each were treated daily with one ounce of stress formula as shown in column 5, Table 5 delivered in a gelatin capsule for two days and 60 calves acting as controls received nothing for prophylaxis. In the test calves one animal died because it had been medicated too late but none of the other test animals exhibited any symptoms of disease. However, the control calves had a 90 percent rate of dysentery which was the same as in previous years. The calves were treated with stress formula immediately after they broke with the dysentery and they cleared up. The new calves in the herd are now being treated with one ounce of stress formula as shown in column 5, Table 5 in gelatin capsules and they showed the same results with one gel cap daily for two days as the test calves. The last twenty calves in the herd that have been treated with the stress formula protocol have been turned out to pasture and are 7% heavier and have better coats and attitude than the test calves. Neighboring ranchers with calves having similar dysentery problems have also started testing the stress formula protocol and have obtained similar successful results.

EXAMPLE 44

A farm in Pennsylvania had 40 ovum donor cows that were losing all their calves and some of the adult cows also appeared ill. The University of Ohio diagnosed the cows and calves as suffering from *Clostridium Perfrengens* type A. The cows and calves were first treated with several available antibiotics with no success. The morbidity rate for the calves was 100% and mortality was 80%. A protocol was begun of treating calves weighing about 80–100 pounds each with one ounce daily of the stress formula as shown in column 5, Table 5 for seven days when they were born. These calves were given no antibiotics. Since the initiation of this protocol approximately 30 calves have been treated, no dysentery has been observed in the herd and no more calves have died.

EXAMPLE 45

A herd of 130 head of cows and calves in Columbus Nebr. was suffering from chronic dysentery of coliform origin. Approximately 60% of the calves appeared affected. Treatment with antibiotics and fluids provided moderate success with an approximate ten percent mortality rate. Ten of the calves weighing about 80–100 pounds each and suffering from the dysentery were then treated daily with one ounce of the stress formula as shown in column 5, Table 5 for three days. After the three days on the protocol the 10 calves no longer exhibited signs of dysentery. However, the untreated calves still had dysentery problems.

EXAMPLE 46

Fifty mares and foals at a farm in Yakama Wash. were infected with *Rhodococcus*. The foals were treated with Azithomycin daily from birth for six weeks along with a plasma infusion at birth and again at 14 days. A study was conducted in which twenty-five foals weighing approximately 110 pounds each were drenched with one ounce of the stress formula as shown in column 5, Table 5 from several hours old for seven days and twenty-five foals that did not receive the stress formula served as controls. The Azithomycin and plasma treatments were halted immediately upon initiation of the stress formula in the animals receiving that formula. The Azithomycin treatment was maintained for the controls. The foals that were drenched with stress formula had an average white blood count of 13,000 at 24 hours of age. The controls had an average of 8,000, indicating a much higher level of immune readiness for the stress formula foals. The stress formula treated foals exhibited a 63% increase in white cell count. The foals were weighed weekly and the test foals were consistently heavier. One case of joint illness and three cases of respiratory problems were observed in the controls after two weeks into the study. No problems were observed with the test foals.

Table C below sets forth the results of a blood test that showed that the administered stress formula and not the elevated response was due to the colostrum from the mare. Usually most of the mare colostrom is no longer absorbed by a foal after 12 hours. This test showed a 63% increase in white count.

TABLE C

|  | BLOOD DRAWN AT BIRTH | BLOOD DRAWN AFTER 28 HOURS |
| --- | --- | --- |
| WBC | 5.7 | 9.3 |
| HCT | 41.1 | 27.6 |

TABLE C-continued

|  | BLOOD DRAWN AT BIRTH | BLOOD DRAWN AFTER 28 HOURS |
| --- | --- | --- |
| BASOPHILS | 0 | 0 |
| EOSINOPHILS | 11 | 0 |
| POLY LYMPHOCYTES | 4220 | 7347 |
| LYMPHOCYTES | 1340 | 1767 |
| MONOCYTES | 129 | 196 |
| FIBRINOGEN | 200 | 200 |

EXAMPLE 47

This study with 300 pigeons shows that the addition of 5.61 gms of stress formula as shown in column 5, Table 5 per of gallon of drinking water per day for seven days dramatically reduced the incidence of circo virus in pigeons. The dosage was given in drinking water and or mixed in food with a moist carrier to 300 pigeons and was consumed by the pigeons in twelve hours. A n average pigeon weighs about 300 gm and the water consumption of a pigeon is about 40 ml per day. Thus each pigeon received dosage of about 1.25 mg of transfer factor in stress formula daily for seven days. After seven days the incidence of circo virus in the 300 pigeons was reduced 40%.

EXAMPLE 48

An 18 year old male pony weighing 500 pounds that was fed 1500 mg of straight Transfer factor in wheat bran for three months showed a low thyroid reading of 9.87 fig and a poor cortisol rhythm of 5%. After receiving 1500 mg of transfer factor, essential fats (20571.88 mg of canola oil, 20571.88 mg of safflower oil and 1,418.75 mg of flax seed oil as shown in Table 2) and 498.72 mg of zinc daily for 8 months, the thyroid level was increased 43% to 14.6 µg and cortisol function was raised to 59%. This shows the synergism of transfer factor, zinc and essential fats in treating hypothyroidism.

EXAMPLE 49

A 20 year old female mare weighing 1000 pounds exhibited a low thyroid reading of 0.9 ug/dl (with 0.9 ug to 2.8 ug being normal) and an inconsistent cortisol rhythm. After being given 1500 mg of transfer factor in a bran carrier for 20 days a second reading at a different lab was taken which showed a thyroid level of 5.6 ng (with 12.0 to 40.0 ng being normal) and a morning cortisol rhythm of 44.7 ng and evening one of 43.6 ng. The horse was then put on 1500 mg of transfer factor with essential fats (20571.88 mg of canola oil, 20571.88 mg of safflower oil and 1,418.75 mg of flax seed oil as shown in Table 2) and 498.72 mg of zinc daily for two months and 10 days. After that time, the blood tests taken showed a 78.5% increase in thyroid function to 11.0 ng and cortisol rhythm improvement from 2% to 51% in normal ranges with readings of 69.8 ng in the morning and 34.3 ng in the evening. The horse has been maintained on this transfer factor, essential fats and zinc regimen and has shown continued clinical improvement with hoof and hair coat indicative of good thyroid function.

EXAMPLE 50

An 8 year old warm blood horse weighing 1200 pounds and suffering from EPM had been on 3000 mg of transfer factor for six weeks with his traditional diet and had shown no clinical improvement. After being administered 5 oz of the premix formula (as shown in column 5, Table 2, except that the amount of transfer factor was 1500 mg instead of 750 mg) daily for 35 days this horse improved 80%. This horse is now being maintained daily on 5 oz of the Premix formula as shown in column 5, Table 2 except that the amount of transfer factor was increased to 1500 mg and has continued to improve.

EXAMPLE 51

Over fifty cases of benign tumors in cats (2.2 gm/daily as shown in column 5, Table 4), dogs (28.37 gm/daily as shown in column 5, Table 3) and horses and cattle (5 oz./daily as shown in column 5, Table 2) have been treated with the premix formulations. These tumors range from benign sarcoids, to pappilomas. In general, the tumors have been reduced from 40% to 80% and and even completely in some cases. Malignant tumors such as oral squamous cell carcinomas have been reduced in dogs receiving 28.37 gm/daily of the premix formula as shown in column 5 of Table 3 and in cats receiving 2.2 gm/daily of the premix formula as shown in column 5 of Table 4.

EXAMPLE 52

An outbreak of PURRS (porcine upper respiratory and reproductive disease in swine) occurred at a swine operation located in Iowa. The outbreak affected thousands of pigs with high mortality and morbidity rate. A set of 6200 pigs, weighing about 12 pounds each, that had just arrived from the farrowing house were dosed daily with 130 g total of transfer factor in 2.86 gms or 0.1 oz of stress formula for four consecutive days in an advanced water metering device. The concentration of the components are the same as shown in column 5, Table 5 except that the concentration of dextrose is 20,825 mg and transfer factor is 1300 mg per ounce of formula. The product was suspended in solution to insure that each pig received an accurate dose when drinking. After 10 days on this protocol all the pigs appeared normal with no indication of PURRS.

EXAMPLE 53

This study involves 132 pigs entering the nursery at a swine farm in Ohio. Sixty-six pigs weighing about 12 pounds each acting as the test group are dosed daily with 300 mg total of transfer factor in divided doses of 150 mg am and pm daily in 0.15 oz or 4.2 gms of stress formula having the same component concentrations as the stress formula in Example 52 for three days. The remaining 66 pigs were the control group and received no medication (antibiotics, stress formula etc.). All the pigs were fed the same diet. After 14 days the test pigs appeared disease free and exhibited better weight gain than the control pigs. Upon slaughter the carcass data shows no liver and kidney disease in the test group but around a 1.5% disease rate in the control group.

EXAMPLE 54

A five year old gelding, weighing about 1000 pound, has chronic laminitis with 5 degree rotation of p-3. This horse is on oat hay and two grams of Butazolidin twice daily, with constant episodes of acute inflammation, ulcerations in the gastrointestinal tract and anemia. Hemoglobin is 11.0 percent. The horse is administered 1500 mg of transfer factor and super oxide dismutase at 6.0 mg per pound of body weight daily for two months. After this time, there is a 50% reduction in the laminitis with a 12% hemoglobin elevation and butazoldin is reduced to one half gram twice daily. The horse no longer appears anemic and has a bright coat and attitude. The ulcerations in the gastrointestinal tract appear healed.

EXAMPLE 55

A fifteen year old horse male, weighing 1000 pounds, with laminitis for five years, re-occurring episodes of inflammation and gastrointestinal ulcerations is given two grams of butazoldin twice daily to control these symptoms. This horse is lame to the extent she is not serviceably sound. The horse is then given a daily treatment of 1500 mg transfer factor and glucosamine salts at a rate of 6.5 mg per pound of body weight for three months. This allows in a reduction of the butazolidin to one half gram twice daily and reduces the ulcerations from the leaky gut syndrome. This horse is 40% improved and capable of light ground pleasure work.

EXAMPLE 56

A ten-year-old mare weighing 1000 pounds, with chronic laminitis is a high level performance horse with slight rotation of p-3. She requires one-half gram of banamine twice daily to perform, is listless and not winning her barrel races and has a poor hoof growth and poor hair coat. The daily administration of transfer factor at 1500 mg along with super oxide dismutase at 6 mg per pound of body weight and 6.5 mg of glucosamine salts per pound of body weight for three months allows the reduction of banamine to 500 mg daily. The leaky gut syndrome symptoms are reduced and this horse is more alert. The horse's performance is 70% improved, and coat and hoof condition is also improved.

EXAMPLE 57

A ten-year-old dog weighing 60 pounds is recovering from surgery on his cruciate ligament repair. This dog has additional hip dysplasia or arthritis of the hip allowing for a very poor recovery period since this dog is on 300 mg of Rymadal daily creating kidney problems and anemia over a five day period of time. Predinisilone at 10 mg/twice daily is depressing the appetite. The administration of 3 grams of transfer factor (dogs) and super oxide dismutase for 21 days with a component concentration as listed in column 5, Table 6, allows for a 10% reduction of Rymadal and predinisilone per day with complete stoppage after 10 days. After 10 days on TF and SOD, the tissue appears healed and the dog's locomotion is 80% improved and his appetite is good.

EXAMPLE 58

One hundred head of cattle weighing 450 pounds arrive in the feedlot from a two-hour truck ride from a ranch and are just weaned off the cows. Fifty of the cattle vaccinated are processed with routine vaccination and worming and one injection of Micotil and act a controls. The other fifty cattle are vaccinated, wormed and each given one ounce of solution containing 1500 mg transfer factor and 1418 mg of lactic acid producing bacteria as shown in Table 5. This dose is given orally to each of the test cattle for four more days. After 30 days on the transfer factor and lactic acid producing bacteria, the test cattle are each 10 pounds heavier than the Micotil cattle.

EXAMPLE 59

Ten kittens are suffering from severe feline pneumonitis. Administration of 234 mg of transfer factor and 255.9 mg of lactic acid producing bacteria as shown in Table 5 for 5 days reduces the feline pneumonitis 60%.

EXAMPLE 60

A small horse ranch had a chronic problem of *Rhodococcus* in all of its foals which weigh about 110 pounds each. Traditional treatment of plasma, azithomycin controls about 60% of the problem. The foals are given 1300 mg of transfer factor and 1418 mg of *lactobacillus acidophilus* as shown in Table 5 daily. This reduces the incidence of *Rhodococcus* to 20% given adjunctively with plasma azithomycin.

EXAMPLE 61

Ten foals are given the transfer factor and *lactobacilllus acidophilus* as in Example 60 but without the azithomycin for 5 days following birth. The incidence of *Rhodococcus* is reduced 60%.

EXAMPLE 62

One Hundred head of cows calving are having a serious outbreak of *Clostridium Perfrengens* type A with a calve morbidity rate of 80% and a mortality rate of 30% given traditional treatment. The calves weighing about 110 pounds each are given 750 mg of transfer factor and 1418 mg of *lactobacillus acidophilus* (109 colony forming units (CFU)/gm) for two consecutive days and the incidence of clostridium is reduced to 20% with mortality reduced to 5%.

EXAMPLE 63

An animal shelter has 80 sick kittens suffering from feline pneumonitis. The incidence of morbidity is 80% with 10% death. The administration daily of 234 mg transfer factor, 51.0 mg yeast, and 255.9 mg lactic acid for 7 days reduces the morbidity to 30% and mortality to 5%.

EXAMPLE 64

Five hundred head of stockers enters the feed lot weighing about 600 pounds each after a 6-hour trailer ride from the ranch and are immediately processed (i.e., wormed and vaccinated). Two hundred fifty head or every other calf is given 750 mg transfer factor, 283 mg yeast, and 2368 mg lactic acid according to Table 5. The other calves are processed and some are given Micotil and others are given Liquarnycin and sulfas to test different products at recommended doses. After 40 days, the transfer factor, yeast, and lactic acid bacteria calves are 12 pounds heavier than the other calves and morbidity is 30% less in the transfer factor, etc., calves than in the other calves. Carcass yield data shows major improvement on the transfer factor cattle with large ribeye, less carcass waste, and higher yield.

EXAMPLE 65

Ten mares on a small ranch have 100% incidence of *Rhodococcus* with annual cost of $1,500 in treatment with plasma and azithomycin. Treatment with plasma and azithomycin is halted and all foals are treated with a drench of one-ounce solution daily for 7 days containing 283 mg yeast, and 1418 mg lactic acid producing bacteria as shown in column 5, Table 5, with 1300 mg of transfer factor. If any foal shows slight signs of infection it is again drenched daily for 7 more days with the transfer factor, yeast and lactic acid producing composition. The foals weigh about 110 pounds each. The incidence of *Rhodococcus* in the foals is reduced 60%.

EXAMPLE 66

A small dairy herd of 100 cows has *Clostridium Perfrengens* type A chronic dysentery in its first born calves. Calves are being lost with conventional treatment. The remaining calves are treated with formula a of 1300 mg transfer factor and 1418 mg lactic acid producing bacteria and 283 mg yeast as shown in Table 5 daily for 5 days after birth, mixing the product into solution and drenching each calf. Morbidity is reduced 60% and mortality reduced 80%.

EXAMPLE 67

A pig farm has a serious outbreak of PURRS disease affecting 60% of the 5000 pig operation. The pigs have many other diseases as a result of the complexity of the PURRS disease. Five thousand new pigs are scheduled to arrive in one week. Each pig is given a 2.8 gm solution containing 130 mg of transfer factor, 283 mg yeast and 1418 mg lactic acid producing bacteria (as shown in Table 5) before they leave the mother. This treatment is continued for 3 more days after they reach the nursery. At the end of this protocol, morbidity from PURRS is reduced 20%.

What is claimed is:

1. A formulation comprising pharmaceutically acceptable transfer factor, zinc, at least one pharmaceutically acceptable essential fatty acid, Vitamin C and a pharmaceutically acceptable yeast, wherein the amount of said transfer factor is from 10 mg to 10,000 mg per ounce of formulation.

2. The formulation of claim 1 further comprising pharmaceutically acceptable ionic salts or chelates of one or more of calcium, phosphorous, selenium, iron, magnesium, manganese, copper, iodine, cobalt and molybdenum.

3. The formulation of claim 2 further comprising pharmaceutically acceptable lactic acid generating bacteria, montmorillonite and Vitamins A, $B_2$, $B_6$, $B_{12}$, E and K.

4. The formulation of claim 3 further comprising pharmaceutically acceptable d-biotin, folic acid, niacin, Vitamin $D_3$, pantothenic acid and thiamine.

5. The formulation of claim 4 further comprising pharmaceutically acceptable lysine, methionine, arginine and methyl sulfonyl methane.

6. A formulation comprising pharmaceutically acceptable transfer factor and a pharmaceutically acceptable lactic acid generating bacteria wherein the amount of said transfer factor is from 10 mg to 10,000 mg per ounce of formulation.

7. The formulation of claim 6 further comprising pharmaceutically acceptable yeast.

8. The formulation of claim 7 further comprising pharmaceutically aeceptable montmorillinite.

9. The formulation of claim 8 further comprising at least one essential pharmaceutically acceptable fatty acid, pharmaceutically acceptable ionic salts or chelates of the elements calcium, phosphorous, selenium, iron, magnesium, manganese, copper, iodine, cobalt and molybdenum, yeast, Vitamins A, $B_2$, $B_6$, $B_{12}$, C, B and K, d-biotin, folic acid, niacin, Vitamin D3, pantothenic acid and thiamine, lysine, methionine, arginine and methyl sulfonyl methane.

10. The formulation of claim 6 further comprising pharmaceutically acceptable ionic salts or chelates of calcium, magnesium, sodium and potassium.

11. The formulation of claim 10 further comprising pharmaceutically acceptable citric acid.

12. The formulation of claim 11 further comprising Vitamins A, $B_2$, $B_6$, $B_{12}$ C, E and thiamine.

13. The formulation of claim 7 further comprising pharmaceutically acceptable ionic salts or chelates of calcium, magnesium, sodium and potassium.

14. The formulation of claim 13 further comprising pharmaceutically acceptable citric acid.

15. The formulation of claim 14 further comprising Vitamins A, $B_2$, $B_6$, $B_{12}$ C, E and thiamine.

* * * * *

UNITED STATES PATENT AND TRADEMARK OFFICE
CERTIFICATE OF CORRECTION

PATENT NO. : 6,962,718 B2
DATED : November 8, 2005
INVENTOR(S) : Joseph C. Ramaekers It is certified that error appears in the above-identified patent and that said Letters Patent is hereby corrected as shown below:

Column 36,
Line 49, change "C, B and K," to -- C, E and K --.
Line 50, change "D3" to -- $D_3$ --.

Signed and Sealed this

Fourth Day of April, 2006

JON W. DUDAS
*Director of the United States Patent and Trademark Office*